(12) United States Patent
Jovanovich

(10) Patent No.: US 12,103,004 B2
(45) Date of Patent: Oct. 1, 2024

(54) METHOD AND APPARATUS FOR PROCESSING TISSUE AND OTHER SAMPLES ENCODING CELLULAR SPATIAL POSITION INFORMATION

(71) Applicant: SILICON VALLEY SCIENTIFIC, INC., Livermore, CA (US)

(72) Inventor: Stevan Bogdan Jovanovich, Livermore, CA (US)

(73) Assignee: SILICON VALLEY SCIENTIFIC, INC., Livermore, CA (US)

( * ) Notice: Subject to any disclaimer, the term of this patent is extended or adjusted under 35 U.S.C. 154(b) by 846 days.

(21) Appl. No.: 16/980,358

(22) PCT Filed: Mar. 12, 2019

(86) PCT No.: PCT/US2019/021942
§ 371 (c)(1),
(2) Date: Sep. 11, 2020

(87) PCT Pub. No.: WO2019/178164
PCT Pub. Date: Sep. 19, 2019

(65) Prior Publication Data
US 2021/0046482 A1    Feb. 18, 2021

Related U.S. Application Data

(60) Provisional application No. 62/670,234, filed on May 11, 2018, provisional application No. 62/641,425, filed on Mar. 12, 2018.

(51) Int. Cl.
| | | |
|---|---|---|
| *B01L 3/00* | (2006.01) | |
| *C12N 15/10* | (2006.01) | |
| *G01N 1/28* | (2006.01) | |
| *G01N 35/00* | (2006.01) | |
| *G01N 35/08* | (2006.01) | |
| *G16B 5/00* | (2019.01) | |

(52) U.S. Cl.
CPC ... *B01L 3/502784* (2013.01); *B01L 3/502761* (2013.01); *B01L 3/50857* (2013.01); *C12N 15/1013* (2013.01); *G01N 1/286* (2013.01); *G01N 35/0099* (2013.01); *G01N 35/08* (2013.01); *G16B 5/00* (2019.02); *B01L 2200/025* (2013.01); *B01L 2200/026* (2013.01); *B01L 2200/027* (2013.01); *B01L 2200/028* (2013.01); *B01L 2200/10* (2013.01); *B01L 2300/0867* (2013.01); *B01L 2300/0893* (2013.01); *B01L 2300/0896* (2013.01); *B01L 2300/18* (2013.01)

(58) Field of Classification Search
CPC ......... B01L 3/502784; B01L 3/502761; B01L 3/50857; B01L 2200/025; B01L 2200/026; B01L 2200/027; B01L 2200/028; B01L 2200/10; B01L 2300/0867; B01L 2300/0893; B01L 2300/0896; B01L 2300/18; B01L 3/5085; B01L 2400/0487; C12N 15/1013; G01N 1/286; G01N 35/0099; G01N 35/08; G01N 1/08; G16B 5/00; C12M 45/02

See application file for complete search history.

(56) References Cited

U.S. PATENT DOCUMENTS

| | | |
|---|---|---|
| 5,234,809 A | 8/1993 | Boom et al. |
| 5,665,554 A | 9/1997 | Reeve et al. |
| 5,898,071 A | 4/1999 | Hawkins |
| 5,952,215 A | 9/1999 | Dwulet et al. |
| 6,190,616 B1 | 2/2001 | Jovanovich et al. |
| 6,534,262 B1 | 3/2003 | McKernan et al. |
| 6,551,839 B2 | 4/2003 | Jovanovich et al. |
| 7,244,961 B2 | 7/2007 | Jovanovich et al. |
| 8,288,106 B2 | 10/2012 | Fekete et al. |
| 8,536,322 B2 | 9/2013 | Han |

(Continued)

FOREIGN PATENT DOCUMENTS

| | | |
|---|---|---|
| EP | 3368668 | 5/2018 |
| WO | 2012138926 A1 | 10/2012 |

(Continued)

OTHER PUBLICATIONS

Siebrasse et al, Reconstitution of nuclear protein exportin isolated nuclear envelopes, 2002, The journal of cell biology, 158, pp. 849-854. (Year: 2002).*
European Patent Office: Supplementary European Search Report for EP19768043, dated Mar. 10, 2022 (Completion Date Nov. 23, 2021), 11 pages.
US Patent Office/U.S. Appl. No. 15/5771,607 Final Office Action, dated Jul. 6, 2020, 29 pages.
US Patent Office/U.S. Appl. No. 15/771,607 Notice of Allowance dated May 13, 2021, 12 pages.
US Patent Office/U.S. Appl. No. 15/771,607 Office Action dated Oct. 4, 2019, 22 pages.

(Continued)

*Primary Examiner* — Narayan K Bhat
(74) *Attorney, Agent, or Firm* — Storella, P.C.

(57) ABSTRACT

Provided herein is a system comprising: a) spatial sampler system configured to collect and transmit one or a plurality of cells or nuclei from a tissue specimen, the system comprising: i) a lower carrier having an array of conduits passing therethrough, each conduit comprising an opening on a first side and communicating with an opening on a second side, wherein the opening on the second side either (1) terminates in a capillary or (2) opens onto a well of a multiwell plate; ii) positioned, above the lower carrier, a perforated specimen holder configured to support a frozen tissue specimen, wherein the specimen holder comprises a plurality of perforations having a size sufficient to permit the passage of single cells or nuclei; and iii) positioned, above the specimen holder, a multifunctional head comprising an upper array of upper conduits, optionally, each aligned with a conduit opening of the lower carrier.

22 Claims, 11 Drawing Sheets

(56) References Cited

U.S. PATENT DOCUMENTS

| | | | |
|---|---|---|---|
| 9,133,511 | B2 | 9/2015 | Ju et al. |
| 9,371,598 | B2 | 6/2016 | Chee |
| 10,830,757 | B2* | 11/2020 | Soper ............... G01N 33/48721 |
| 11,111,487 | B2 | 9/2021 | Jovanovich et al. |
| 2002/0078778 | A1 | 6/2002 | Grover et al. |
| 2003/0170617 | A1 | 9/2003 | Pasloske |
| 2004/0033168 | A1 | 2/2004 | Hughes et al. |
| 2008/0286161 | A1 | 11/2008 | Heaney et al. |
| 2010/0126286 | A1 | 5/2010 | Self et al. |
| 2011/0092376 | A1 | 4/2011 | Colston et al. |
| 2011/0196663 | A1 | 8/2011 | Doyle et al. |
| 2011/0287951 | A1* | 11/2011 | Emmert-Buck ... C12N 15/1006 536/25.4 |
| 2012/0228142 | A1 | 9/2012 | Sibbett et al. |
| 2013/0109024 | A1 | 5/2013 | Rajagopalan et al. |
| 2013/0190212 | A1 | 7/2013 | Handique et al. |
| 2014/0066318 | A1 | 3/2014 | Frisen et al. |
| 2014/0228255 | A1 | 8/2014 | Hindson et al. |
| 2015/0148239 | A1 | 5/2015 | Peter et al. |
| 2016/0253584 | A1 | 9/2016 | Fodor et al. |
| 2017/0136458 | A1 | 5/2017 | Dunne et al. |
| 2018/0305681 | A1* | 10/2018 | Jovanovich .......... C12Q 1/6806 |
| 2022/0033802 | A1 | 2/2022 | Jovanovich et al. |
| 2024/0026338 | A1 | 1/2024 | Jovanovich et al. |

FOREIGN PATENT DOCUMENTS

| | | |
|---|---|---|
| WO | 2014135232 A1 | 9/2014 |
| WO | 2014210225 A1 | 12/2014 |
| WO | 2017075293 A1 | 5/2017 |
| WO | 2018102471 A1 | 6/2018 |
| WO | 2019178164 A1 | 9/2019 |

OTHER PUBLICATIONS

US Patent Office/U.S. Appl. No. 15/771,607, Restriction Requirement dated Apr. 18, 2019, 7 pages.
US Patent Office: U.S. Appl. No. 17/381,796 Final Office Action dated Sep. 21, 2022; 23 pages.
US Patent Office: U.S. Appl. No. 17/381,796 Office Action dated Feb. 16, 2022, 20 pages.
European Patent Office, Communication Pursuant to Article 94(3) EPC, dated Jun. 1, 2021, 4 pages.
International Searching Authority/US International Search Report for International Patent Application No. PCT/US16/59232, dared Mar. 2, 2017, 5 pages.
US Patent Office/ U.S. Appl. No. 17/381,796, Notice of Allowance dated Feb. 1, 2023.
Crosetto, "Spatially resolved, transcriptomics and beyond", Nature Review Genetics, Jan. 1, 2015, pp. 57-66, Retrieved from the Internet: URL:http://www.nature.com/nrg/journal/v16/n1/pdf/nrg3832.pdf.
European Patent Office; "Extended European Search Report and European Search Opinion", Feb. 4, 2019, 7 pages.
International Searching Authority/US "International Search Report and Written Opinion" for PCT/US19/21942, dated Jul. 15, 2019, 14 pages.
International Searching Authority/US "International Search Report and Written Opinion" for PCT/US16/59232, dated Mar. 2, 2017, 7 pages.
Je Hyuk Lee et al., "Fluorescent in situ sequencing (FISSEQ) of RNA for gene expression profiling in intact cells and tissues", Nature Protocols, vol. 10, No. 3, Feb. 12, 2015, p. 442-458.
K. H. Chen et la, "Spatially resolved, highly multiplexed RNA profiling in single cells", Science, vol. 348, No. 6233, Apr. 9, 2015, pp. aaa6090-aaa1116090.
Kjetil Hodne et al.> "Single-Cell Isolation and Gene Analysis: Pitfalls and Possibilities", International Journal of Molecular Sciences, vol. 16. No. 11, Nov. 10, 2015, pp. 26832-26849.
Macosko et al., Highly Parallel Genome-wide Expression Profiling of Individual Cells Using Nanoliter Droplets. Cell May 21, 2016 vol. 161 No. 5 pp. 1202-1214. Especially p. 1203 fig 1A; p. 1205 fig 2A, B.
Nature Biotechnology 33.5 (2015): 503; 9 pages (Year: 2015).
Pereira et al. Development of Automated Processing of Tissue for Single Cell and Nuclei for Genomic Applications. AGBT meeting, Feb. 2018 [online]. [Retrieved Jun. 24, 2019]. Retrieved on the internet: . Especially col. 2 para 4.
Armani et al. "2D-PCR: a method of mapping DNA in tissue sections", Lab on a Chip, dated Dec. 2, 20091, 19 pages.
European Patent Office; Partial Supplementary Search Report (R164 EPC) for EP 19768043.2, dated Dec. 3, 2021; 12 pages.
US Patent Office Non-Final Office Action for U.S. Appl. No. 18/200,569 dated Mar. 28, 2024, 25 pages.

* cited by examiner

METHOD AND APPARATUS FOR PROCESSING TISSUE AND OTHER SAMPLES ENCODING CELLULAR SPATIAL POSITION INFORMATION

CROSS REFERENCE TO RELATED APPLICATIONS

This application claims the benefit of the priority date of provisional patent application, 62/641,425, filed Mar. 12, 2018, entitled, "Method and apparatus for processing tissue and other samples encoding cellular spatial position information", and of provisional patent application 62/670,234 filed May 11, 2018, entitled "Method and apparatus for encoding cellular spatial position information", the contents of all are incorporated herein in their entirety.

STATEMENT OF FEDERALLY SPONSORED RESEARCH OR DEVELOPMENT (IF ANY)

None.

THE NAMES OF THE PARTIES TO A JOINT RESEARCH AGREEMENT IF THE CLAIMED INVENTION WAS MADE AS A RESULT OF ACTIVITIES WITHIN THE SCOPE OF A JOINT RESEARCH AGREEMENT

None.

REFERENCE TO A "SEQUENCE LISTING"

None.

BACKGROUND OF THE INVENTION

A) Field of Invention

This invention relates to the field of sample preparation from biological materials. More specifically, the invention relates to the processing of solid tissues into single cells, nuclei, biomolecules, and processed samples for bioanalysis.

B) Description of Related Art

Analysis of single cells and groups of cells is now beginning to provide information to dissect and understand how cells function individually and unprecedented insight into the range of individual responses aggregated in ensemble measurements. Single cell methods for electrophysiology, flow cytometry, imaging, mass spectrometry (Lanni, E. J., et. al. J Am Soc Mass Spectrom. 2014; 25(11):1897-907.), microarray (Wang L and K A Janes. Nat Protoc. 2013; 8(2):282-301.), and Next Generation Sequencing (NGS) (Saliba A. E., et. al. Nucleic Acids Res. 2014; 42(14):8845-60.) have been developed and are driving an increased understanding of fundamental cellular processes, functions, and interconnected networks. As the individual processes and functions are understood and differentiated from ensemble measurements, the individual information can in turn lead to discovery of how network processes among cells operate. The networks may be in tissues, organs, multicellular organisms, symbionts, biofilms, surfaces, environments, or anywhere cells interact.

Next Generation Sequencing (NGS) of single cells is rapidly changing the state of knowledge of cells and tissue, discovering new cell types, and increasing understanding of the diversity of how cells and tissue function. Single cell NGS RNA sequencing (Saliba A. E., et. al., Nucleic Acids Res. 2014; 42(14):8845-60.) (Shapiro E. et. al., Nat Rev Genet. 2013; 14(9):618-30.) is unveiling the complexity of cellular expression, and the heterogenity from cell to cell, and from cell type to cell type (Buettner F. et. al., Nat Biotechnol. 2015; 33(2):155-60.). In situ sequencing (Ke R et. al., Nat Methods. 2013; 10(9):857-60.), (Lee J H, et. al., Nat Protoc. 2015; 10(3):442-58.) (Lee J H, et. al., Science. 2014, 21; 343(6177):1360-3.) has shown the feasability of directly sequencing of fixed cells. However, for RNA, many fewer reads are generated with in situ sequencing, biasing against detection of low abundant transcripts. Photoactivatable tags have been used to capture mRNA from single cells (Lovatt, D., et. al., Nat Methods. 2014; 11(2):190-6.) from known location in tissue, albeit with low throughput capture and manual cell collection.

The NGS market has grown explosively over the last 10 years with costs reductions and throughput increases exceeding Moore's law. The applications have expanded from whole genome sequencing to RNA-Seq, ChIP-Seq, exome sequencing, to now single-cell sequencing, single nuclei sequencing, and many other exciting applications. The power and low cost of NGS is broadly changing life sciences and moving into translational medicine and the clinic as precision medicine begins. Until recent years essentially all of the NGS analysis was of 'bulk samples' where the nucleic acids of numerous cells had been pooled. There is a need for systems that integrate the sample preparation of single-cell suspensions, and single-cell libraries, and bulk libraries starting from original unprocessed specimens.

Single-cell sequencing is rapidly changing the state of knowledge of cells and tissue, discovering new cell types, and increasing the understanding of the diversity of how cells and tissue function. Single-cell RNA sequencing (Shapiro E. Biezuner T, Linnarsson S. Single-cell sequencing-based technologies will revolutionize whole-organism science. Nat Rev Genet. 2013; 14(9):618-30. PMID: 23897237) has highlighted the complexity of cellular expression, and the large heterogeneity from cell-to-cell, and from cell type-to-cell type (Buettner F. Natarajan K N, Casale F P, Proserpio V, Scialdone A, Theis F J, Teichmann S A, Marioni J C, Stegle O. Computational analysis of cell-to-cell heterogeneity in single-cell RNA-sequencing data reveals hidden subpopulations of cells. Nat Biotechnol. 2015; 33(2):155-60. PMID: 25599176). Single-cell sequencing (Wang., Y. and N. E. Navin. Advanced and Applications of single-cell sequencing technologies. Molecular Cell. 2015. 58:598-609. PMID 26000845.) is being applied to development, brain structure and function, tumor progression and resistance, immunogenetics, and more.

Single cell nucleic acid sequencing technology and methods using NGS and Next Next Generation Sequencing (NNGS), such as nanopores, are rapidly evolving. Common components are incorporation of a marker or barcode for each cell and molecule, reverse transcriptase for RNA sequencing, amplification, and pooling of sample for NGS and NNGS (collectively termed NGS) library preparation and analysis. Starting with isolated single cells in wells, barcodes for individual cells and molecules have been incorporated by reverse transcriptase template switching before pooling and polymerase chain reaction (PCR) amplification (Islam S. et. al. Genome Res. 2011; 21(7):1160-7.) (Ramsköld D. et. al. Nat Biotechnol. 2012; 30(8):777-82.) or on a barcoded poly-T primer with linear amplification (Hashimshony T. et. al. Cell Rep. 2012 Sep. 27; 2(3):666-73.) and unique molecular identifiers (Jaitin D. A. et. al. Science. 2014; 343(6172):776-9.).

Pioneering work has used the power of nanodroplets to perform highly parallel processing of mRNA from single cells with reverse transcription incorporating cell and molecular barcodes from freed primers (inDrop) (Klein A. M. et. al. Cell. 2015, 161(5):1187-201.) or primers attached to paramagnetic beads (DropSeq) (Macosko E. Z. et. al. Cell. 2015; 161(5):1202-14.) and using micronozzles such as described by them or Geng T. et. al. Anal Chem. 2014; 86(1):703-12 or others; the lysis conditions and reverse transcriptase described by (Fekete R. A. and A. Nguyen. U.S. Pat. No. 8,288,106. Oct. 16, 2012) are incorporated by reference cited therein are incorporated by reference, including instrumentation, chemistry, workflows, reactions conditions, flowcell design, and other teachings. Both inDrop and DropSeq are scalable approaches have change the scale from 100s of cells previously analyzed to 1,000s and more.

Single-cell sequencing is now providing new information to biologists, genomic scientists, and clinical practitioners, and the single-cell market is growing explosively, perhaps the next great disruption in life sciences and medicine. Multiple companies are providing systems to take single-cell suspensions and create Single-cell RNA sequencing (scRNA-Seq), ATAC-Seq, targeted, and other libraries that are analyzed by the robust NGS sequencing and analysis pipeline. No system integrates the upstream process to produce single-cell suspensions for NGS single-cell sequencing or has integrated from tissue to single-cell libraries.

The production of single-cells or nuclei or nucleic acids from solid and liquid tissue is usually performed manually with a number of devices used without process integration. A combination of gentle mechanical disruption with enzymatic dissociation has been shown to produce single-cells with the highest viability and least cellular stress response (Quatromoni J G, Singhal S, Bhojnagarwala P, Hancock W W, Albelda S M, Eruslanov E. An optimized disaggregation method for human lung tumors that preserves the phenotype and function of the immune cells. J Leukoc Biol. 2015 January; 97(1):201-9. doi: 10.1189/jlb.5TA0814-373. Epub 2014 Oct. 30.).

Many manual protocols for dissociating different tissues exist, for example, Jungblut M., Oeltze K., Zehnter I., Hasselmann D., Bosio A. (2009). Standardized Preparation of Single-Cell Suspensions from Mouse Lung Tissue using the gentleMACS Dissociator. JoVE. 29, doi: 10.3791/1266; Stagg A J, Burke F, Hill S, Knight S C. Isolation of Mouse Spleen Dendritic Cells. Protocols, Methods in Molecular Medicine. 2001: 64: 9-22. Doi: 10.1385/1592591507.; Lancelin, W., Guerrero-Plata, A. Isolation of Mouse Lung Dendritic Cells. J. Vis. Exp. (57), e3563, 2011. DOI: 10.3791/3563; Smedsrod B, Pertoft H. Preparation of pure hepatocytes and reticuloendothelial cells in high yield from a single rat liver by means of Percoll centrifugation and selective adherence. J Leukocyte Biol. 1985: 38: 213-30.; Meyer J, Gonelle-Gispert C, Morel P, Bühler L Methods for Isolation and Purification of Murine Liver Sinusoidal Endothelial Cells: A Systematic Review. PLoS ONE 11(3) 2016: e0151945. doi:10.1371/journal.pone.0151945.; Kondo S. Scheef E A, Sheibani N, Sorenson C M. "PECAM-1 isoform-specific regulation of kidney endothelial cell migration and capillary morphogenesis", Am J Physiol Cell Physiol 292: C2070-C2083, (2007); doi: 10.1152/ajpcell.00489.2006., Ehler, E., Moore-Morris, T., Lange, S. Isolation and Culture of Neonatal Mouse Cardiomyocytes. J. Vis. Exp. (79), e50154, doi:10.3791/50154 (2013).; Volovitz I Shapira N, Ezer H, Gafni A, Lustgarten M, Alter T, Ben-Horin I, Barzilai O, Shahar T, Kanner A, Fried I, Veshchev I, Grossman R, Ram, Z. A non-aggressive, highly efficient, enzymatic method for dissociation of human brain-tumors and brain-tissues to viable single cells. BMC Neuroscience (2016) 17:30 doi: 10.1186/512868-016-0262-y; F. E Dwulet and M. E. Smith, "Enzyme composition for tissue dissociation," U.S. Pat. No. 5,952,215, Sep. 14, 1999.

For example, solid tissue of interest is usually dissected and then minced into 1-5 mm pieces by hand or a blender type of disruptor is used. Enzymes or a mixture of enzymes, such as collagenases, hydrauronadase, papain, proteases, DNase, etc., are added and the specimen incubated, typically with shaking or rotation to aid dissociation to prepare single cells or nuclei from tissue. In many procedures, the specimen is titurated multiple times or mechanically disrupted. The mechanical disruption may be through orifices, grinding, homogenization, forcing tissue through screens or filters, sonication, blending, bead-beating, rotors with features that dissociate tissue, and other methods to physically disrupt tissue to help produce single cells.

Following dissociation, in some embodiments the dissociated sample is passed through a filter, such as a 70 micron filter, to retain clumps of cells or debris. The filtrate which contains single cells or nuclei may be further processed to change the media or buffer; add, remove, or deactivate enzymes; concentrate cells or biomolecules, lyse red blood cells, or capture specific cell types. The processing typically involves multiple steps of centrifugation and resuspension, density gradients, or magnetic bead capture of specific cell types using antibodies or other affinity capture ligands, or fluorescent cell-activated sorting (FACS). The titer and viability of the single-cell suspension is usually determined using optical imaging with a microscope and haemocytometer, or an automated instrument. In many cases, the viability is determined using Trypan blue or fluorescent dyes. Quality control can include characterization of the nucleic acids by gel electrophoresis on an instrument such as a BioAnalyzer, or the determination of the expression of certain genes using reverse transcripatase and quantitative polymerase chain reaction (RT-qPCR), or other relevant methods.

The rapid production of nuclei can give a snapshot of gene expression (Habib N, Li Y, Heidenreich M, Swiech L, Avraham-Davidi I, Trombetta J J, Hession C, Zhang F, Regev A. Div-Seq: Single-nucleus RNA-Seq reveals dynamics of rare adult newborn neurons. Science. 2016 Aug. 26; 353(6302):925-8. doi: 10.1126/science.aad7038. Epub 2016 Jul. 28.; Grindberg R V, Yee-Greenbaum J L, McConnell M J, Novotny M, O'Shaughnessy A L, Lambert G M, Araúzo-Bravo M J, Lee J, Fishman M, Robbins G E, Lin X, Venepally P, Badger J H, Galbraith D W, Gage F H, Lasken R S. RNA-sequencing from single nuclei. Proc Natl Acad Sci USA. 2013 Dec. 3; 110(49):19802-7. doi: 10.1073/pnas.1319700110. Epub 2013 Nov. 18.).

The production of nuclei from tissue can be performed using a Dounce homogenizer in the presence of a buffer with a detergent that lyses cells but not nuclei. Nuclei can also be prepared starting from single cell suspensions (CG000124_SamplePrepDemonstratedProtocol_-_Nuclei_RevB, 10× Genomics, assets.contentful.com/an68im79xiti/6FhJX6yndYy0OwskGmMc8I/48c341c178feafa3ce21f 5345ed3367b/CG000124_SamplePrepDemonstratedProtocol_-_Nuclei_RevB.pdf) by addition of a lysis buffer such as 10 mM Tris-HCl, 10 mM NaCl, 3 mM MgCl2 and 0.005% Nonidet P40 in nucleasefree water and incubation for 5 min on ice before centifugation to pellet the nuclei followed by resuspension in a resuspension buffer such as 1×PBS with 1.0% BSA and 0.2 U/µl RNase Inhibitor. The nuclei may be repeatedly pelleted and resuspended to purify them or density gradients or other purification methods used. The titer and viability of the nuclei suspension is usually determined using optical imaging with a microscope and haemocytometer, or an automated instrument with viability determined using Trypan blue or fluorescent dyes.

The multi-process workflow to produce and characterize single-cells and nuclei from tissue is a usually performed manually using several devices without process integration, limiting the scalablity of single cell sequencing and the integration with downstream processes to create a sample-to-answer system. It is laborious and requires skilled technicians or scientists, and results in variability in the quality of the single-cells, and, therefore, in the downstream libraries, analysis, and data. The multiple steps and skill required can lead to differing qualities of single cells or nuclei produced even from the same specimen. Today, the production of high quality single-cells can take months of optimization.

Standarization is necessary before routine single-cell preparation can be performed, particularly in clinical settings. In addition, the length of the process and the process of dissociation can lead to the tissue and cells changing physiology such as altering their expression of RNA and proteins in response to the stresses of the procedure, accentuated by potentially long processing times. A crucial recent insight is that cell processing methods can alter gene expression by placing cells under stress. For example, the use of protease to dissociate cells from tissue, confounding analysis of the true transcriptome (Lacar B, Linker S B, Jaeger B N, Krishnaswami S, Barron J, Kelder M, Parylak S, Paquola A, Venepally P, Novotny M, O'Connor C, Fitzpatrick C, Erwin J, Hsu J Y, Husband D, McConnell M J, Lasken R, Gage F H. Nuclear RNA-seq of single neurons reveals molecular signatures of activation. Nat Commun. 2016 Apr. 19; 7:11022. doi: 10.1038/ncomms11022. PMID: 27090946.).

Robust, automated sample preparation is required to simplify workflows before full integration can be achieved with downstream NGS analysis to produce true sample-to-answer systems in the future. Robust processes are required that will input a wide range of tissues from a wide range of organisms and tissues and produce high-quality single-cell or nuclei suspensions without intervention, at acceptable viability for suspensions, with minimal changes to gene expression patterns.

To achieve a standardized process will require a system that automates the sample preparation of cells or nuclei (e.g., single cells or single nuclei) from tissue with a single-use disposable cartridge. In some cases, microvalves can be used in cartridges. Microvalves are comprised of mechanical (thermopneumatic, pneumatic, and shape memory alloy), non-mechanical (hydrogel, sol-gel, paraffin, and ice), and external (modular built-in, pneumatic, and non-pneumatic) microvalves (as described in: C. Zhang, D. Xing, and Y. Li., Micropumps, microvalves, and micromixers within PCR microfluidic chips: Advances and trends. Biotechnology Advances. Volume 25, Issue 5, September-October 2007, Pages 483-514; Diaz-Gonzalez M., C. Fernandez-Sanchez, and A. Baldi A. Multiple actuation microvalves in wax microfluidics. Lab Chip. 2016 Oct. 5; 16(20):3969-3976.; Kim J., Stockton A M, Jensen E C, Mathies R A. Pneumatically actuated microvalve circuits for programmable automation of chemical and biochemical analysis. Lab Chip. 2016 Mar. 7; 16(5):812-9. doi: 10.1039/c51c01397f; Samad M F, Kouzani A Z. Design and analysis of a low actuation voltage electrowetting-on-dielectric microvalve for drug delivery applications. Conf Proc IEEE Eng Med Biol Soc. 2014; 2014:4423-6. doi: 10.1109/EMBC.2014.6944605.; Samad M F, Kouzani A Z. Design and analysis of a low actuation voltage electrowetting-on-dielectric microvalve for drug delivery applications. Conf Proc IEEE Eng Med Biol Soc. 2014; 2014:4423-6. doi: 10.1109/EMBC.2014.6944605.; Lee E, Lee H, Yoo S I, Yoon J. Photothermally triggered fast responding hydrogels incorporating a hydrophobic moiety for light-controlled microvalves. ACS Appl Mater Interfaces. 2014 Oct. 8; 6(19): 16949-55. doi: 10.1021/am504502y. Epub 2014 Sep. 25.; Liu X, Li S. An electromagnetic microvalve for pneumatic control of microfluidic systems. J Lab Autom. 2014 October; 19(5):444-53. doi: 10.1177/2211068214531760. Epub 2014 Apr. 17; Desai A V, Tice J D, Apblett C A, Kenis P J. Design considerations for electrostatic microvalves with applications in poly(dimethylsiloxane)-based microfluidics. Lab Chip. 2012 Mar. 21; 12(6):1078-88. doi: 10.1039/c21c21133e. Epub 2012 Feb. 3.; Kim J, Kang M, Jensen E C, Mathies R A Lifting gate polydimethylsiloxane microvalves and pumps for microfluidic control. Anal Chem. 2012 Feb. 21; 84(4):2067-71. doi: 10.1021/ac202934x. Epub 2012 Feb. 1; Lai H, Folch A. Design and dynamic characterization of "single-stroke" peristaltic PDMS micropumps. Lab Chip. 2011 Jan. 21; 11(2):336-42. doi: 10.1039/c01c00023j. Epub 2010 Oct. 19).

Fluidic connections between cartridges and the instrument fluidics can be achieved by the use of spring-loaded connectors and modular microfluidic connectors as taught by Jovanovich, S. B. et. al. Capillary valve, connector, and router. Feb. 20, 2001. U.S. Pat. No. 6,190,616 and Jovanovich; S. B. et. al. Method of merging chemical reactants in capillary tubes, Apr. 22, 2003, U.S. Pat. No. 6,551,839; and Jovanovich, S., I. Blaga, and R. McIntosh. Integrated system with modular microfluidic components. U.S. Pat. No. 7,244,961. Jul. 17, 2007. which are incorporated by reference and their teachings which describe the modular microfluidic connectors and details of modular microfluidic connectors, including their use as multiway valves, routers, and other functions including microfluidic circuits to perform flowthrough reactions and flow cells with internally reflecting surfaces.

The surface chemistries of the paramagnetic beads and conditions to bind cells or precipitate, wash, and elute nucleic acids and other biomolecules onto surfaces is well understood, (Boom, W. R. et. al. U.S. Pat. No. 5,234,809. Aug. 10, 1993.), (Reeve, M. and P. Robinson. U.S. Pat. No. 5,665,554. Sep. 9, 1997.), (Hawkins, T. U.S. Pat. No. 5,898,071. Apr. 27, 1999.), (McKernan, K. et. al. U.S. Pat. No. 6,534,262. Mar. 18, 2003.), (Han, Z. U.S. Pat. No. 8,536,322. Sep. 17, 2013.), (Dressman et al., "Transforming single DNA molecules into fluorescent magnetic particles for detection and enumeration of genetic variation" Proc. Natl. Acad. Sci. 100(15):8817-8822 (2003)), (Ghadessy et al., "Directed evolution of polymerase function by compartmentalized self-replication", Proc. Natl. Acad. Sci. 98(8): 4552-4557 (2000)), (Tawfik and Griffiths, "Man-made cell-like compartments for molecular evolution" Nat. Biotech. 16(7):652-656 (1998)), (Williams et al., "Amplification of complex gene libraries by emulsion FOR" Nat. Meth. 3(7): 545-550 (2006)), and many chemistries are possible and within the scope of the instant disclosure.

Analysis of single cells is revealing how cells function individually and in groups, and unprecedented insight into the range of cellular behavior, until now aggregated in averaged ensemble measurements. Single cell analysis methods for electrophysiology, flow cytometry, imaging, mass spectroscopy (Lanni E J, Dunham S J, Nemes P, Rubakhin S S, and Sweedler J V. J Am Soc Mass Spectrom. 2014 November; 25(11):1897-907), microarray (Wang L, Janes K A. Nat Protoc. 2013 February, 8(2):282-301.), and NGS sequencing (Klein A M, Mazutis L, Akartuna I, Tallapragada N, Veres A, Li V, Peshkin L, Weitz D A, Kirschner M W. Cell. 2015 May 21; 161(5):1187-201; Macosko E Z, Basu A, Satija R, Nemesh J, Shekhar K, Goldman M, Tirosh I, Bialas A R, Kamitaki N, Martersteck E M, Trombetta J J, Weitz D A, Sanes J R, Shalek A K, Regev A, McCarroll S A. Cell. 2015 May 21; 161(5):1202-14.) are enabling an increased understanding of fundamental cellular processes and functions.

Single cell RNA-Seq (Saliba A E, Westermann A J, Gorski S A, Vogel J. Nucleic Acids Res. 2014 August; 42(14):8845-60; Buettner F, Natarajan K N, Casale F P, Proserpio V, Scialdone A, Theis F J, Teichmann S A, Marioni J C, Stegle O. Nat Biotechnol. 2015 February; 33(2):155-60.) is unveiling the complexity of gene expression, and heterogenity from cell-to-cell and from celltype-to-celltype. Pioneering work used nanodroplets to perform highly parallel single-cell mRNA processing with reverse transciptase incorporating cell and molecular barcodes from freed primers (inDrop) (Klein A M, et al., Cell. 2015 May 21, 161(5):1187-201. or primers attached to paramagnetic beads (DropSeq) (Macosko E Z, et al. Cell. 2015 May 21; 161(5):1202-14.). These methods change the experimental scale from 100s of cells to greater than 1,000,000 (support.10xgenomics.com/single-cell/datasets). However, all these systems lose spatial information of the location of each individual cell (or groups of cells) in a microenvironment.

In situ sequencing has shown the feasability of directly sequencing fixed cells (Ke R, et al., Nat Methods. 2013 September; 10(9):857-60; Lee J H, Daugharthy E R, Scheiman J, Kalhor R, Yang J L, Ferrante T C, Terry R, Jeanty S S, Li C, Amamoto R, Peters D T, Turczyk B M, Marblestone A H, Inverso S A, Bernard A, Mali P, Rios X, Aach J, Church G M. Science. 2014 Mar. 21; 343(6177):1360-3.; Lovatt D, Ruble B K, Lee J, Dueck H, Kim T K, Fisher S, Francis C, Spaethling J M, Wolf J A, Grady M S, Ulyanova A V, Yeldell S B, Griepenburg J C, Buckley P T, Kim J, Sul J Y, Dmochowski I J, and J Eberwine. Nat Methods. 2014 February; 11(2):190-6.).

ReadCoor has developed a Fluorescent in situ Sequencing (FISSEQ) instrument for in situ sequencing of tissue sections (World Wide Web site: readcoor.com). However, in situ RNA sequencing does not utilize the well developed NGS infrastructure and fewer reads may bias against detecting low abundant transcripts. Nanostring has launched Spatial Genomics which deposits photolabile probes for mRNA or antibodies for protein detection. The instrument optically scans the tissue and selectively releases the probes with a UV laser from regions of interest before capillary transfer of the released probes into a microtiter plate. One limitation is that it only detects the probes that interrogate the tissue and therefore will not discover any new or rare transcripts. (Moncada et al bioRxiv (January 26) 2018; D01:10.1101/254375). Chen K H, Boettiger A N, Moffitt J R, Wang S, Zhuang X. Science. 2015 Apr. 24; 348(6233).). Multiple chromatin accessibility assays have been developed including scNMT-seq (Clark S J, Argelaguet R, Kapourani C A, Stubbs T M, Lee H J, Alda-Catalinas C, Krueger F, Sanguinetti G, Kelsey G, Marioni J C, Stegle O, Reik W. sNat Commun. 2018 Feb. 22, 9(1):781.), ATAC-Seq (Buenrostro, J D, Giresi, P. G., Zaba L. C., Chang, H. Y.& Greenleaf, W. J. Nature Methods 10, 1213-1218 (2013)), and FAIRE-Seq (Bianco S, Rodrigue S, Murphy B D, Gevry N. Methods Mol Biol. 2015; 1334:261-72.). Preissl et. al. recently demonstrated snATAC-Seq with single nuclei from flash-frozen tissue, albeit without spatial barcodes (Preissl S, Fang R, Huang H, Zhao Y, Raviram R, Gorkin D U, Zhang Y, Sos B C, Afzal V, Dickel D E6, Kuan S, Visel A, Pennacchio L A, Zhang K, Ren B1. Nat Neurosci. 2018 Feb. 12. doi: 10.1038/s41593-018-0079-3.). None of the methods, technologies, or products utilize the full potential of the NGS infrastructure to create high-resolution, high-throughput 3D tissue maps from single nuclei. There are now multiple ways to perform single nuclei DNA sequencing including a well based approach to perform $\phi29$ amplification followed by targeted amplification (Leung M L, Wang Y, Kim C, Gao R, Jiang J, Sei E, Navin N E. Nat Protoc. 2016 February; 11(2):214-235; Leung, M L, Y. Wang, J. Waters, and N E Navin. Genome Biol. 2015; 16(1): 55.).

DNA methylation (5mC) is an epigenetic modification with important regulatory roles. The bisulfite method is well established to discriminate between cytosine and 5-methyl-cytosine (Luo C, Keown C L, Kurihara L, Zhou J, He Y, Li J, Castanon R, Lucero J, Nery J R, Sandoval J P, Bui B, Sejnowski T J, Harkins T T, Mukamel E A, Behrens M M, Ecker J R. Science. 2017 Aug. 11, 357(6351):600-604.) and oxidative bisulfite (Booth M J, Branco M R, Ficz G, Oxley D, Krueger F, Reik W, Balasubramanian S. Science. 2012 May 18; 336(6083):934-7.) sequencing can help establish the methylome.

The pioneering work of the Boyden lab has demonstrated expansion microscopy where tissue is expand about four-fold using an acrylamide polymerization without distortion of cellular and subcellular structures (Chen, F., P W. Tillberg and Edward S. Boyden. Science. 2015 Jan. 30; 347(6221): 543-548).

BRIEF SUMMARY OF THE INVENTION

High-throughput data-driven science has given researchers powerful tools to analyze cells, tissues, and organisms including tools to analyze single cells and nuclei. Systems for preparing sequencing samples at the single cell and single nuclei level are now commercially available, connected to the Next Generation Sequencing (NGS) pipeline. The throughput of the NGS systems is enormous and the experimental pipeline is well integrated after processing of cell suspensions through library preparation, sequencing, and bioinformatics. However, for NGS data, the original spatial registration of single cells—where the single cells were found, who their neighbors were, and what the microenvironment was—is usually completely lost.

This invention enables the development and deployment of novel high-throughput spatial systems that enable construction of 3-D maps at single-cell resolution of biomolecules and nucleic acid sequence data from human and other tissues, leveraging the existing NGS infrastructure. The systems will first be used to analyze the spatial distribution of genomic data from nuclei with single-cell resolution from animal and human solid tissue developed for a spatial single nuclei sequencing, ssnRNA-Seq, application. Additional applications covering genomic, epigenomic, proteomic analyses can be developed and deployed on this systems platform.

The Spatial Sequencer enables low- or high-throughput automated systems that collect nuclei by 'microregions' (a 'spatial pixel', e.g., around 2, 10, or 150 micron dia.) in known order from solid tissue sections. The microregions are spatially-encoded for single nuclei or single cell NGS by adding DNA barcodes, or for proteomics by adding mass tags or other markers. For sequencing, after processing by the existing single cell and nuclei informatics pipeline, spatial software will decode single nuclei or single cells into single microregions, construct spatial representations of the data, cluster the data with other components and analyze 3D and multidimension images of multicomponent gene expression or genetic changes in tissue, at single nuclei resolution. The data can be formatted into standardized open data formats for the deposition and storage of data according to standards and compatible with tools for visualizing, searching, and modeling spatial data.

In one embodiment, the Spatial Sequencing system can be comprised of a Spatial Sampler module that processes solid tissue into nuclei or single cells with a known spatial registration and a Spatial Encoder module that adds DNA or other tags to biomolecules from single nuclei or single cells. The systems will process frozen tissue microtome slices using a disposable cartridge. The cartridge may contain the encoding materials to signal the biomolecules' origin. Multiple sections will be processed to obtain 3D mapping information.

A low throughput Spatial Sequencing system can 1) Process microregions to generate single nuclei or single cells in known spatial order in boluses, 2) Add a spatial nucleic acid barcode (and cell and molecule barcodes) to single nuclei or single cells in nanodroplets, boluses, or nanowells to encode the physical origin, 3) Translate the mRNA into cDNA with an integrated spatial barcode, and 4) Process the data to map tissue for ssnRNA-Seq and share the findings. The system can be expanded to high throughput, and additional applications and capabilities added including fluorescent imaging of tissue sections.

The Spatial Sequencer is a platform designed to deploy multiple applications that preserve spatial information from solid tissues—gene expression, proteomics, DNA sequencing, lncRNA, epigenomics, methylomics, and almost all other NGS applications—for medical, health, life science research, and other applications. For proteomics and metabolomics, the Spatial Sampler module can process the microregions individually and encode mass standards in known order to the nuclei or to the cellular fluids with the nuclei or single cells removed; MS analysis in either known order or with mass standards (which could be DNA barcodes) can reconstruct the 3D physical coordinates of the proteome or metabolome of the microregions from the tissues. The invention includes MS interfaces adaption of the system to MS and other analytical modalities.

The spatial system enabled herein will give researchers, and ultimately clinicians, a fundamentally new high-resolution, high-throughput, high content capability to characterize single cells, place those data in a geo-located context, revealing the spatial relationships between cells, and how each cell functionally and physically relates to their near neighbors in the microenvironments. For ssnRNA-Seq, the system will encode the positional coordinates of the tissue microsample into spatial DNA barcodes.

The spatial system will process microregions of ca. 10-100 micron dia. or larger or smaller sizes from solid tissue into spatially encoded information, allowing analysis of small groups or single nuclei by changing the capillary size or expanding the tissue. The microregions can also be preprocessed with spatial information encoded for MS or metabolics. Microregion resolution will provide valuable granular insight into actual cell types, groupings, infiltration, and function in normal and diseased microenvironments. The microregion approach is readily adaptable to sparse high-resolution sampling or to very dense readouts. Microregions can also be split between types of analyzes to provide multidimensional insight, which is hard to do with a single cell.

This invention has fundamental innovations in encoding spatial position information for single nuclei. Compared to in situ sequencing, this system applies the full power of NGS analysis. This allows the full range of epigenomic assays to be applied and the use of complementary sequencing platforms, such as the Pac Bio that can recognize a wide range of modified nucleic acids.

The technical innovations this invention enables include: 1) Converting flash frozen tissue into single nuclei or single cells to be spatially mapped by microregions in known order in a scalable tissue mapping system that enables the NGS infrastructure to be quickly applied to understanding tissue structure, function, development, and disease progression, 2) Processing tissue by microregions to encode spatial position with mass and other tags for proteomics, metabolics, and cellomics, 3) expanding tissue to manipulate space for single nuclei spatial sequencing, 4) Integrating the workflow to automate specimen processing.

The Spatial Sequencer can incorporate multiple applications such as single cell DNA sequencing, targeted sequencing, fluorescent tagging and imaging to define areas to be sampled, and extending the workflow to integrate downstream library preparation. An array of technologies for single cell and nuclei biomolecular analysis can be adapted to this platform.

The invention enables processing frozen tissue into nuclei or single cells in a flow stream or on a surface in known spatial order by microregions. The direct processing of solid tissue into nuclei or single cells is compatible with flash frozen tissue, cryopreserved tissue, and fresh tissue. Processing into nuclei can eliminates the tissue-by-tissue and species-by-species method variations to process solid tissue into single cells.

The spatial technology approach enables many different embodiments and a scaleable instrument, software, chemistry, and disposable cartridges. The system can use a three-axis robot and on-instrument fluidics to process solid tissues into single nuclei spatially encoded libraries. The system can have two main modules which are developed in parallel and then integrated in one embodiment. In this embodiment, the Spatial Sampler module can accept fresh, frozen, formalin fixed parafin embedded (FFPE), or other tissue on cartridge and converts 1 or more, or 96, or 384 or more microregions into nuclei suspensions that are separated into boluses or nanowells. When the region of interest is in position, the sampler head (part of a multifunctional head) can seals an upper bundle of, for example, 96 conduits, which may be capillaries, microchannels, tubing, etc. on the tissue and generate boluses of nuclei in a lower bundle of 96 conduits. For the Spatial Encoder module, commercial single cell encapsulation hardware simplifies the encoder to developing spatially encoded beads and integrating delivery of the beads to boluses with the nozzle fluidics by either timing for open loop or optical detection for closed loop operation.

The Spatial Sequencer system is an integrated and automated sample-to-spatially encoded library system that a specialist can operate to prepare fresh or frozen tissue specimens into libraries for NGS analysis to detect nucleic acids and other biomolecules. In one embodiment, an automated low-throughput spatial system can have automated 'spatial sampling' to collect microregions in known order from solid tissues, barcoding the spatial location into DNA for ssnRNA-Seq analysis, and Integration of sampling and barcoding modules.

In one embodiment, frozen mouse and rat tissue is processed a single microregion at a time into nuclei in a flow and delivering it to a single microfluidic nozzle for scRNA-Seq. The processing can be scaled up to process 12 or 24 or 96 or more microregions in parallel. An automated low throughput prototype-level system to encode the spatial position of tissue for spatial single nuclei RNA-Seq is described.

High-throughput spatial sequencing systems with additional capabilites for imaging, fluid delivery of stains and other reagents to the tissue, and other applications including methylation, barcoded antibodies, and chromatin access applications, as well as epigenomic, proteomic, metabolimic, and systems biology, and other applications are also possible and examples enabled herein.

In one aspect provided herein is a system comprising: a) spatial sampler system configured to collect and transmit one or a plurality of cells or nuclei from a tissue specimen, the system comprising: i) a lower carrier having an array of conduits passing therethrough, each conduit comprising an opening on a first side of the lower carrier and communicating with an opening on a second side, wherein the opening on the second side of the lower carrier either (1) terminates in a capillary or (2) opens onto a well of a multiwell plate; ii) positioned, above the lower carrier, a perforated specimen holder configured to support a frozen tissue specimen, wherein the specimen holder comprises a plurality of perforations having a size sufficient to permit the passage of single cells or nuclei; and iii) positioned, above the specimen holder, a multifunctional head comprising an upper array of upper conduits, optionally, each aligned with a conduit opening of the lower carrier. In one embodiment, the openings on the top side of the lower carrier are configured as wells that communicate with narrower conduits. In another embodiment, the openings on the top side of the lower carrier have a diameter of about 2 µm to about 150 µm e.g., about 100 microns. In another embodiment, the conduits are selected from capillaries, microchannels, tubing, and electrowetting conduits. In another embodiment, a plurality of the conduits each have different lengths, wherein the lengths are determined based on relative spatial position of the conduits in the array. In another embodiment, the lower conduits communicate with a common fluid conduit. In another embodiment, the lower conduits are mated with nozzles leading to a common conduit. In another embodiment, the lower conduits each communicate with a different well or set of wells of a multiwell plate. In another embodiment, the specimen holder comprises a mesh, e.g., a stainless-steel mesh, polymer mesh, metal mesh, strainer, or filter. In another embodiment, the perforations have a diameter of about 20 µm to about 100 µm, e.g., about 20 µm to about 50 µm or about 50 µm to about 100 µm, e.g. about 30 microns. In another embodiment the system further comprises a cryopreserved tissue specimen in the specimen holder. In another embodiment, the multifunctional head has an array of between 12 and 96 conduits. In another embodiment the upper array of conduits is ganged fluidically to a syringe pump configured to deliver one or more solutions (nuclei isolation solution, tissue disruption solution to produce single cells, emulsion oil, or cleaning solution) to a microregion on the specimen carrier. In another embodiment, the system comprises a container of a tissue disruption solution comprising one or more collagenases and/or one or more proteinases and/or a nuclei isolation solution comprising a chemical that disrupts cell membranes, e.g., comprising a detergent. In another embodiment, the system comprises a temperature controller to control temperature of the specimen holder. In another embodiment, the temperature controller comprises a Peltier. In another embodiment, the multifunctional head comprises at least any of 1, 12, 24, 96, 384 conduits. In another embodiment, the multifunctional head is configured to deliver nuclei isolation solution through the conduits to a tissue specimen positioned on the specimen support. In another embodiment, the multifunctional head is configured to deliver pressure and/or vacuum to the conduits. In another embodiment the system further comprises a movable arm operatively attached to a motor and controlled by a computer (e.g., a robot) that moves the multifunctional head along any dimension of a three-dimensional axis. In another embodiment the system further comprises a motor that moves the multifunctional head along a direction substantially perpendicular to a plane of the specimen carrier, e.g., so as to sandwich a specimen held by the sample carrier between the lower carrier and conduits in the multifunctional head. In another embodiment the system further comprises a computer comprising a processor and memory including code that, when executed by the processor, controls the movement of the multifunctional head and the delivery of pressure or vacuum through the upper conduits. In another embodiment the system further comprises a motor that moves the sample carrier in an X-Y plane parallel to a face of the multifunctional head. In another embodiment, the multifunctional head comprises an imaging station configured to image a specimen on the sample carrier. In another embodiment, the multifunctional head further comprises a dispense head configured to dispense liquids, e.g., imaging reagents or dissociation or other solutions, onto the biological specimen. In another embodiment, the transfer head comprises a plurality of extraction channels where in the extraction channels are arrayed in a two dimensional array (e.g., a line) or a three-dimensional array (e.g., a plane). In another embodiment, the spatial encoder subsystem comprises a plurality of fluidic channels that merge into the encoder channel in which each has an inlet configured to receive the microsamples from an extraction channel. In another embodiment, the transfer membranes have attached thereto a plurality of capture elements, each capture element comprising a particle, which is optionally paramagnetic, having attached thereto one or more antibodies that bind cells in the biological specimen, and nucleic acid markers comprising positional barcodes comprising spatial information where the spatial information identifies the position of the particle on the transfer membranes on the multifunctional head. In another embodiment, the nucleic acid markers further comprise cell markers identifying the cell to which particle binds, and/or molecular barcodes that differently label different nucleic acid molecules and a single cell. In another embodiment, the nucleic acid markers further comprise cell markers identifying the cell to which particle binds, and/or molecular barcodes that differently label different nucleic acid molecules and a single cell, and the particle comprises a capture sequence such as polyT with a spatial barcode. In another embodiment the system further comprises: b) a spatial encoder subsystem configured to perform a series of biochemical reactions on an emulsion comprising microdrops produced by the spatial sampler system, wherein the spatial encoder subsystem comprises: i) a reaction device comprising an inlet configured to receive microdrops from the spatial sampler subsystem, at least one reaction chamber, and an outlet; ii) a reagent rail communicating with the reaction device through a microchannel and comprising reagent sufficient to perform at least one of biochemical reaction on analytes in the microdrops; iii) one or more pumps configured to move the reagents from the reagent rail through the microchannel to the reaction chamber of the reaction device; and iv) optionally, one or more detectors to sense bolus or fluids to control merging of reagents and specimen. In another embodiment, the spatial sampler system and the spatial encoder subsystem are configured as fluidically communicating modules in the system. In another embodiment, the spatial encoder subsystem further comprising: v) a temperature controller configured to control temperature in the reaction chamber. In another embodiment, the spatial encoder subsystem further comprising: v) a magnet configured to reversibly immobilize paramagnetic particles contained in the reaction chamber. In another embodiment, the biochemical reactions comprise reverse transcription of messenger RNA into cDNA encoding the spatial information. In another embodiment, the biochemical reactions comprise at least: (i) reverse transcription of messenger RNA into cDNA; and (ii) amplification of cDNA. In another embodiment, the biochemical reactions comprise at least: (i) primer extension of a primer hybridized to a DNA template to create an extension product; and (ii) amplification of the extension product.

In another aspect provided herein is a method comprising: a) providing a frozen biological tissue specimen on a sample carrier, wherein cells in the tissue sample have a spatial position in the tissue specimen, and wherein the sample carrier comprises (i) a perforated support that supports the tissue specimen and (ii) an array of passages at addressable positions through the sample carrier and positioned below the perforated support; b) disrupting cells in the tissue specimen to release one or a plurality of cells or nuclei; and c) collecting a microsample comprising one or a plurality of released cells or nuclei through the perforations into the passages, wherein the addressable position of a passage indicates the original spatial position of the cell or nucleus moved into the passage. In one embodiment, collecting comprises moving cells or nuclei by force, e.g., by pressure, exerted by a liquid, into the passages. In another embodiment the method comprises collecting cells or nuclei from at least one, a plurality, at least 96 or at least 384 different microregions in the tissue specimen. In another embodiment single cells or nuclei are collected per passage. In another embodiment single cells or nuclei are collected into passages from a microregion in the tissue specimen having a largest dimension of about 20 microns to about 150 microns. In another embodiment the method further comprises determining biomolecular information (e.g., proteomic information, nucleic acid sequence information, epigenetic (e.g., methylation pattern, chromatin accessibility, proximal DNA interactions, etc.) from the nuclei collected in each passage. In another embodiment the method further comprises creating a 2-D or 3-D map of the tissue specimen indicating spatial position of biomolecular information (e.g., proteomic information, nucleic acid sequence information, epigenetic) of the tissue. In another embodiment the method further comprises: sectioning a frozen tissue specimen into a plurality of slices; processing each slice according to operation (a) through (c); generating biomolecules from one or more microregions of each slice; and producing a 3-D reconstruction of spatial position of the information in the original tissue specimen. In another embodiment the method further comprises encoding biomolecules collected from each spatial position with positional information tags that indicate the original spatial position of the biomolecules in the tissue specimen. In another embodiment the information tag is a barcoded antibody, a barcoded oligonucleotide or a mass tag. In another embodiment disrupting tissue into one or a plurality of cells or nuclei comprises delivering to the tissue specimen on the platform a nuclei isolation solution (i.e., a solution that disrupts cell membranes, e.g., comprising a detergent) or a tissue disruption solution that produces single cells. In another embodiment the solution is delivered through an array of capillaries positioned above the specimen carrier. In another embodiment the solution is delivered to each of a plurality of microregions, and single cells or nuclei are collected from the microregion, in sequence. In another embodiment disrupting cells comprises physical disruption. In another embodiment the method further comprises delivering collected single cells or nuclei in boluses into a single flow stream, wherein a position of a bolus in a train of boluses in the flow stream depends on the original spatial position of the single cells or nuclei in the bolus in the tissue specimen. In another embodiment the method comprises collecting a single cell nucleus from each microregion. In another embodiment the method further comprises: d) delivering collected cells or nuclei into wells of a multiwell plate, wherein the position of the wells into which cells or nuclei are delivered depends on the original spatial position of the cells or nuclei in the bolus in the tissue specimen. In another embodiment the method further comprises: d) contacting a collected microsample with a solid particle (e.g., a bead) having attached thereto an oligonucleotide comprising an amplification primer and oligonucleotide barcode sequence, wherein the barcode sequence provides information about the original spatial position of the cells or nuclei in the microsample in the tissue specimen. In another embodiment the method further comprises: d) contacting a collected microsample with a transposon comprising spatial barcodes, which spatial barcodes provide information about the original spatial position of the cells or nuclei in the microsample in the tissue specimen. In another embodiment the method further comprises: d) encapsulating single collected cells or nuclei in low melting point gel beads. In another embodiment the method further comprises: d) treating collecting nucleic acids in the cells or nuclei with bisulfite and determining methylation patterns of the bisulfite-treated DNA.

In another aspect provided herein is method comprising using the system of claim 1 to entrain in a fluidic stream a plurality of microsamples from a biological specimen, wherein the microsamples are contained in spatially separated microdrops or boluses in the fluidic stream and positioned in an order based on their original spatial position within the biological specimen. In one embodiment, the method comprises: a) providing a biological specimen; b) collecting microsamples from one or each of a plurality of different spatial positions in the biological specimen; c) introducing the microsamples in a predetermined order into a fluidic stream in a fluidic channel; d) dividing the fluidic stream into microdrops by introducing boluses of immiscible liquid into the fluidic channel, whereby the microsamples are incorporated into microdrops that are spatially separated from each other in the fluidic stream. In another embodiment the method further comprises: (i) introducing into the fluidic stream a plurality of different spatial markers encoding spatial information, wherein the different spatial markers are incorporated into different microdrops in the fluidic stream, thereby encoding each microdrop with spatial information.

In another aspect provided herein is an article comprising a carrier or cartrdige comprising an array of nanowells, each nanowell comprising an oligonucleotide barcode encoding relative position of the nanowell in the array, wherein the oligonucleotide is attached to a wall of the nanowell or to a solid particle comprised in the nanowell. In one embodiment, each nanowell is configured to hold no more than any of 1, 2, 3, 4, 5, 6, 7, 8, 9 or 10 individual nuclei or no more than any of 1, 2, 3, 4, 5, 6, 7, 8, 9 or 10 individual cells. In another embodiment the carrier comprises an array of at least any of 500, 1000 1500, 2000 or 2500 nanowells.

In another aspect provided herein is a method comprising: a) providing a frozen tissue specimen on a support mesh; b) freeing one or a plurality of cells or nuclei from cells in the tissue specimen while maintaining their spatial relationship; c) moving the freed nuclei into a train or solid support whereby their spatial information is maintained.

In another aspect provided herein is a method comprising: a) providing a frozen biological tissue specimen on a sample carrier, wherein cells in the tissue specimen have a spatial position in the tissue specimen; b) delivering, with a microsyringe, tissue disruption solution and or nuclei isolation solution to a microregion of the tissue specimen to release one or a plurality of cells or nuclei; c) collecting, with a microsyringe, a microsample comprising one or a plurality of released cells or nuclei; and d) moving the microsyringe with the microsample to a well of multiwell plate or to a spatial encoder module and delivering the cells or nuclei in the microsample. In one embodiment, the microsyringe is controlled by a robotic device. In another embodiment the microsyringe contains spatial barcodes attached to a microsyringe barrel or plunger, or on beads preloaded into the microsyringe or picked up after collection of the microsample and then delivered to a nanodroplet generator.

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION OF THE INVENTION

Figure 1:
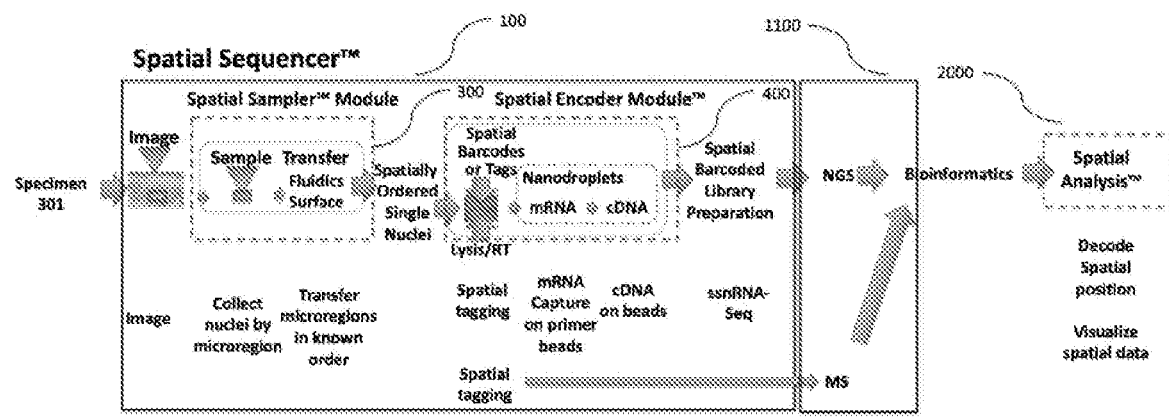
FIG. 1 shows a Spatial Sequencer system, including a spatial sampling module and a spatial encoder module, workflows, and applications to process specimens or tissue specimens into biocomponents such as single cells or nuclei encoding spatial position in the bioanalysis.

Machines and methods useful in executing inventions as described herein are disclosed in WO 2017/075,293, published May 4, 2017 ("Method and apparatus for encoding cellular spatial information") and WO 2018/102,471, published Jun. 7, 2018 ("Method and apparatus for processing tissue samples"), the contents of which are incorporated herein in their entirety.

NGS, mass spectrometry, FACS, and other modern high-throughput analysis systems have revolutionized life and medical sciences. The progression of information has been from the gross level of organism, to tissue, and now to single cell analysis. Single cell analysis of genomic, proteomic including protein expression, carbohydrate, lipid, and metabolism of individual cells is providing fundamental scientific knowledge and revolutionizing research and clinical capabilities.

Specimen: The term "specimen," as used herein, refers to an in vitro cell, cell culture, virus, bacterial cell, fungal cell, plant cell, bodily sample, or tissue sample that contains genetic material. In certain embodiments, the genetic material of the specimen comprises RNA. In other embodiments, the genetic material of the specimen is DNA, or both RNA and DNA. In certain embodiments the genetic material is modified. In certain embodiments, a tissue specimen includes a cell isolated from a subject. A subject includes any organism from which a specimen can be isolated. Non-limiting examples of organisms include prokaryotes, eukaryotes or archaebacteria, including bacteria, fungi, animals, plants, or protists. The animal, for example, can be a mammal or a non-mammal. The mammal can be, for example, a rabbit, dog, pig, cow, horse, human, or a rodent such as a mouse or rat. In particular aspects, the tissue specimen is a human tissue sample. The tissue specimen can be liquid, for example, a blood sample, red blood cells, white blood cells, platelets, plasma, serum. The specimen, in other non-limiting embodiments, can be saliva, a cheek, throat, or nasal swab, a fine needle aspirate, a tissue print, cerebral spinal fluid, mucus, lymph, feces, urine, skin, spinal fluid, peritoneal fluid, lymphatic fluid, aqueous or vitreous humor, synovial fluid, tears, semen, seminal fluid, vaginal fluids, pulmonary effusion, serosal fluid, organs, bronchio-alveolar lavage, tumors, frozen cells, or constituents or components of in vitro cell cultures. In other aspects, the tissue specimen is, without limitation, a solid tissue sample or a frozen tissue sample or a formalin fixed parafin embedded (FFPE) tissue sample or a cryopreserved tissue sample or a biopsy sample such as a fine needle aspirate or a core biopsy or a resection or other clinical or veternary specimen. In still further aspects, the specimen comprises a virus, bacteria, or fungus. The specimen can be an ex vivo tissue or sample or a specimen obtained by laser capture microdissection. The specimen can be a fixed specimen, including as set forth by U.S. Published Patent Application No. 2003/0170617 filed Jan. 28, 2003.

Conduits can be comprised of single capillaries, 3D printed cartridges, microchannels, tubing, microchips, fluidic connections, valves, routers, and other fluidics for flowthrough and nanowell approaches.

Bulk analysis is used to describe the analysis of a pool of analyte from more than one single cell or nucleus; for example, RNA-Seq is bulk analysis as distinct from scRNA-Seq analysis. Similarly, bulk sample preparation refers to sample preparation of samples that have pooled single cells and nuclei.

In some embodiments, the single cells can be analyzed further for biomolecules including one or more polynucleotides or polypeptides or other macromolecules. In some embodiments, the polynucleotides can include a single-stranded or double-stranded polynucleotide. In some embodiments, the polypeptide can include an enzyme, antigen, hormone or antibody. In some embodiments, the one or more biomolecules can include RNA, mRNA, cDNA, DNA, genomic DNA, microRNA, long noncoding RNA, ribosomal RNA, transfer RNA, chloroplast DNA, mitochondrial DNA, or other nucleic acids including modified nucleic acids and complexes of nucleic acids with proteins or other macromolecules.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

The Spatial Sequencer 100, as illustrated in one embodiment in FIG. 1, is a platform technology for spatially encoding biomolecules for readout by analytical platforms including NGS and MS. A low throughput embodiment for spatial single nuclei RNA-Seq with Spatial Sampler 300 and Spatial Encoder 400 modules is described as well as high throughput embodiments with imaging, library preparation, and additional genomic and proteomic applications. This low throughput system embodiment can process tissue into samples that have encoded the spatial position information for single nuclei or single cell RNA-Seq, ATAC-Seq, or many other single cell or nucleus, and bulk applications.

a. Spatial Sampler.

Referring to FIG. 1, the Single Cell Spatial Analysis System 100 accepts specimens 301 and processes one or more microsamples 125 from selected microregions 304 to encode the physical location of the microsample 125 within the specimen 301 to produce spatially encoded single cells or nuclei 1000 in microdrops, e.g., nanodroplets or boluses, by adding a marker such as a DNA barcode that encodes for the location of the microsample 125. Known markers are added in known order to ordered microsamples 125 to encode the spatial position. Analysis method 1100, such as DNA sequencing, mass spectrometry, or other analytical methods, generates single cell analytical data 1600, such as DNA sequence or proteomics, and also decodes the encoded spatial information to produce decoded single cell spatial information 1500. Multiple sample preparation and analytical methods can be used on a specimen. In some aspects where the biomolecules are nucleic acids, the downstream processes can include without limitation, nucleic acid sequencing, targeted resequencing, genotyping analysis, mutation analysis, copy number variation assessment, allele frequency assessment, plasmid construction, cloning, and the like. The decoded single cell spatial information 1500 identifies the spatial position 130 where microsample 125 originated in specimen 301. The single cell analytical data 1600 is analyzed by single cell spatial analysis 2000 software to produce single cell spatial information 3000 which has the analytical data and associated physical position information of the microsample 125.

Figure 2:
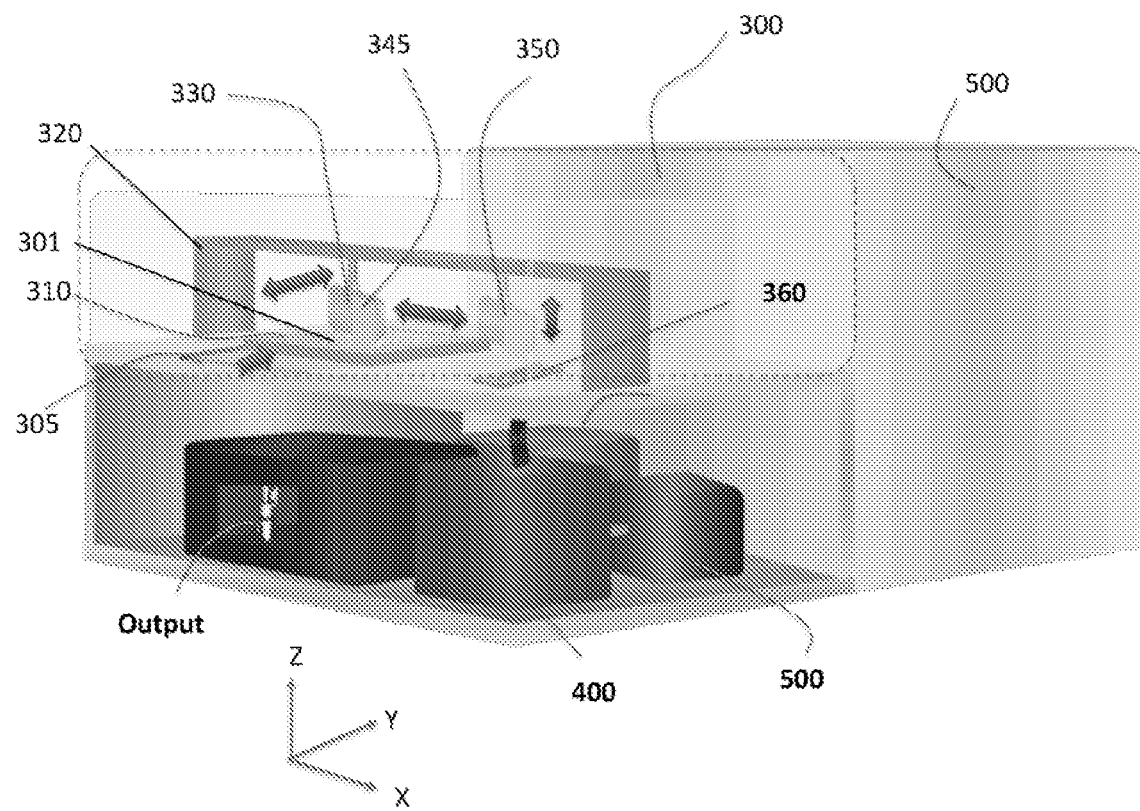
FIG. 2 shows a Single Cell Spatial Analysis System configured for production of nucleic acid spatial libraries.

Referring to FIG. 2, in an embodiment, configured for nucleic acid analysis, specimen 301 is placed in a specimen holder 310 which is inserted into the Spatial Sampler module 300 by loading mechanism 305. Specimen holder 310 may be temperature controlled, critical for cryosections. The loading mechanism can have a mechanical slide, stage, pneumatic actuator, or other mechanism, that accepts specimen holder 310 and moves it into the Single Cell Analysis System 100, either automated or manually, into a fixed position in the Spatial Sampler module 300 or other mechanism. Spatial Sampler module 300 can have a three axis stage 320 that moves a multifunctional head 330 in the x, y and z directions to collect microsamples 125 in a spatially defined manner from specimen 301 at capture position 345 and dispenses the collected microsamples 125 at dispense position 350 into input device 360. In some embodiments the fluidics of the Single Cell Spatial Analysis System 100 are incorporated onto cartridge(s) 4000, described later.

Figure 3:
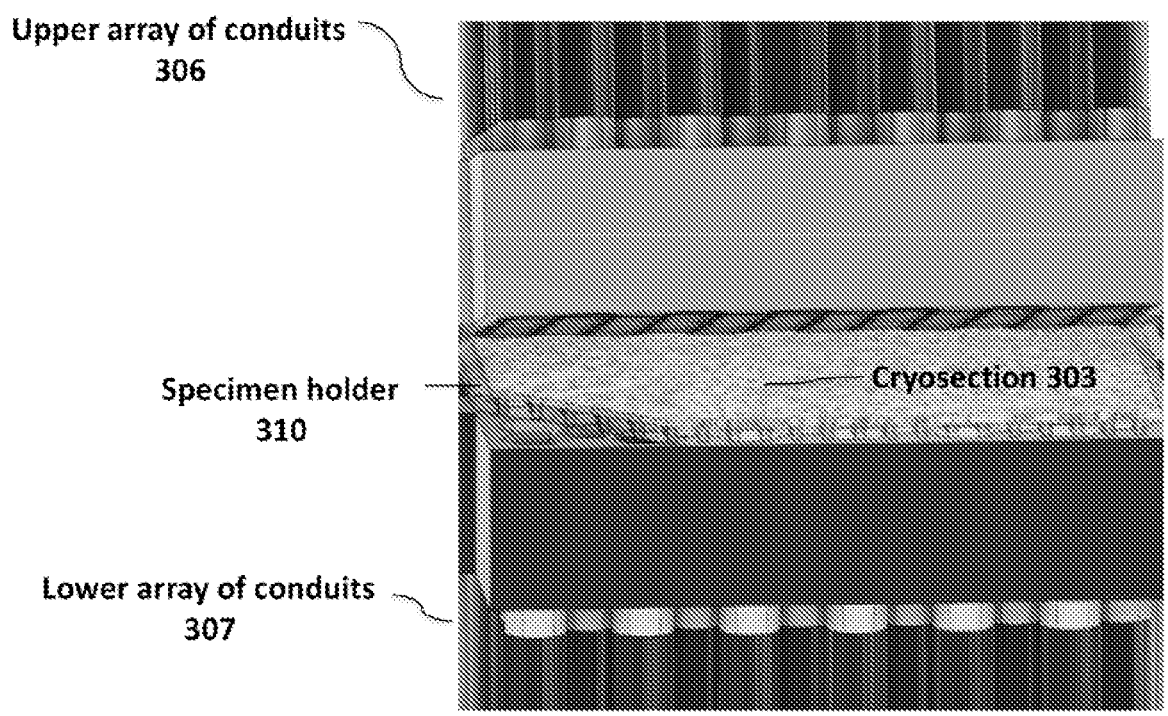
FIG. 3 shows a closeup showing the mating of a sampler head and tissue on a stainless-steel mesh carrier over a lower array. The upper array is tilted for the illustration.

Referring to FIG. 3, in one embodiment, microregions 304 are mechanically defined by the upper array of fluidic conduits 306 of a sampler head (FIG. 3) and then fluidically injected into a lower array of fluidic conduits 307 and into a fluidic stream for downstream nanodroplet or into an array of nanowells 320 for spatial encoding of single nuclei or single cells. Other alternative embodiments include micro-punching the microregions and using pick-and-place robotics to sort the microregions into microtiter or other multiwell plates.

In an embodiment, a fully integrated low throughput spatial system can process cryosections into single nuclei spatially encoded cDNA, ready for processing into a NGS library. In another embodiment, a fully integrated low throughput spatial system can process cryosections 303 into single cells and produce spatially encoded cDNA, ready for processing into a single cell NGS library. In other embodiments, the approach is applied to cellomics and proteomics by adding barcoded antibodies or mass tagged internal standards with collaborators. To scale encoding, a commercial single channel micronozzle can be adapted to inject, e.g., 12 spatial barcoded beads at the proper timing to encode 12 microregions, allowing 8 micronozzles (one run on many systems) to process 96 microsamples.

Spatial Sampler Technology to Generate Nuclei from Microregions of Frozen Tissue Sections.

Figure 4:
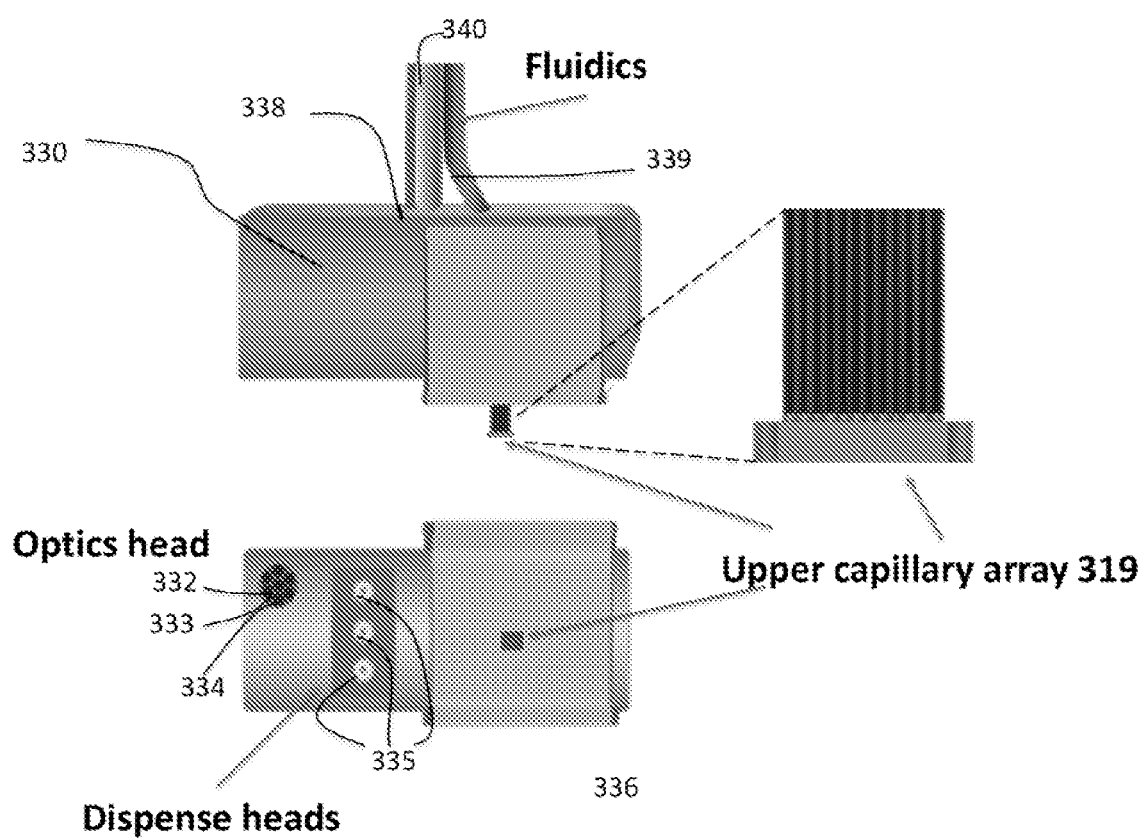
FIG. 4 shows a multifunctional head, side and bottom views, with detail of the array.
Figure 5:
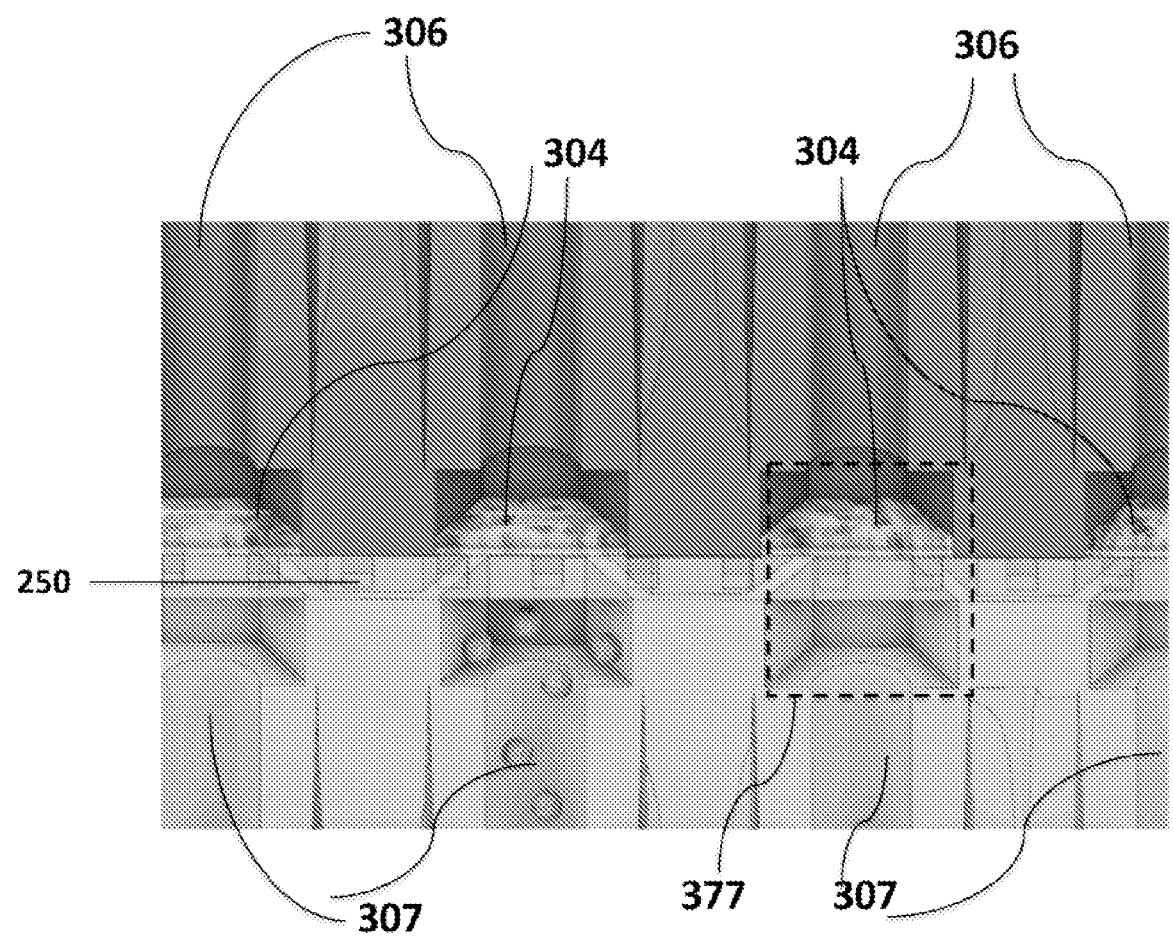
FIG. 5 shows a concept of a single microregion being processed with an interweaving with the microregion to maximize coverage.

The Spatial Sampler module 300 can process a cryosection 303 into cell or nucleus suspensions from separate microregions in known order either into boluses 308 or into nanowells 319. As shown in FIG. 4, in one embodiment, the Spatial Sampler module 300 can have a moveable multifunctional head 330 that can be moved by a two-axis stage to regions of interest to sample. In one embodiment, the multifunctional head 330 will have an array of conduits, e.g., 24 capillaries, ganged fluidically to a syringe pump that can delivers solutions (nuclei isolation solution, dissociation solutions to produce cells, emulsion oil, or cleaning solution) to the section on a specimen holder 310 (FIG. 3), e.g., a stainless steel mesh carrier 250, as shown in FIG. 5, through a disposable matched array of openings in the multifunctional head (above) and lower carrier (below) (together forming an 'eggcrate' 377) that defines the microregions 304.

In one embodiment, the module can work as follows. Referring to FIG. 3 and FIG. 5, A cryosection 303 on a specimen holder 310 which may be a disposable carrier in a cartridge is input on a temperature-controlled two-axis stage and positioned over a lower array of conduits 307 which may be an array of capillaries 318. The specimen holder 310 can be a perforated substrate 250, e.g., a mesh or strainer mesh comprising metal, stainless steel, plastic, polymeric, fiber, or other meshes with pore sizes preferably greater than 5 microns to an embodiment at 30 microns to over 70 microns, or strainer with pores between about 20 µm to about 50 µm, e.g. about 30 µm for nuclei or about 50 µm to about 100 µm, e.g. about 70 microns for cells, or adjusted to the specimen tissue type and process.

The stage moves the section below the multifunctional head 330. The multifunctional head 330 will then lower an upper array of conduits 306, for example, capillaries (e.g., 100 micron ID/176 micron OD (Polymicro, 106815-1818, TSP300665), over the region of interest to match the lower array of conduits 307, sandwiching the cryosection 303 on mesh 250 between the upper and lower arrays of conduits. In one embodiment, the upper array of conduits 306 defines the microregions 304 as it is lowered onto cryosection 303.

The terms upper array of conduits 306 and lower array of conduits 307 may also refer to a single upper or lower or both conduits.

In an embodiment, the upper and lower conduits may align to microns, such as less than 25 microns, and be in close to exact alignment. In an exact alignment, fluid paths from each conduit upper array of conduits 306 through cryosection 303 on specimen holder 310 into the lower array of conduits 307 are direct, once the cryosection 303 or specimen 301 has dissociated the tissue in each microregion 304 into single cells or nuclei, and the fluid flows from the upper array of conduits 306 directly into the lower array of conduits 307.

The movement of upper array of conduits 306 and lower array of conduits 307 need not be exact; in some embodiments; for example without limiting, since the upper array of conduits 306 in the described embodiment defines the microregions 304 as it is lowered onto cryosection 303, and in some embodiments the specimen 301 is dissociated into an array of nanowells 320 and the absolute position of the array of nanowells 320 need not exactly match with the upper array of conduits 306.

Figure 6:
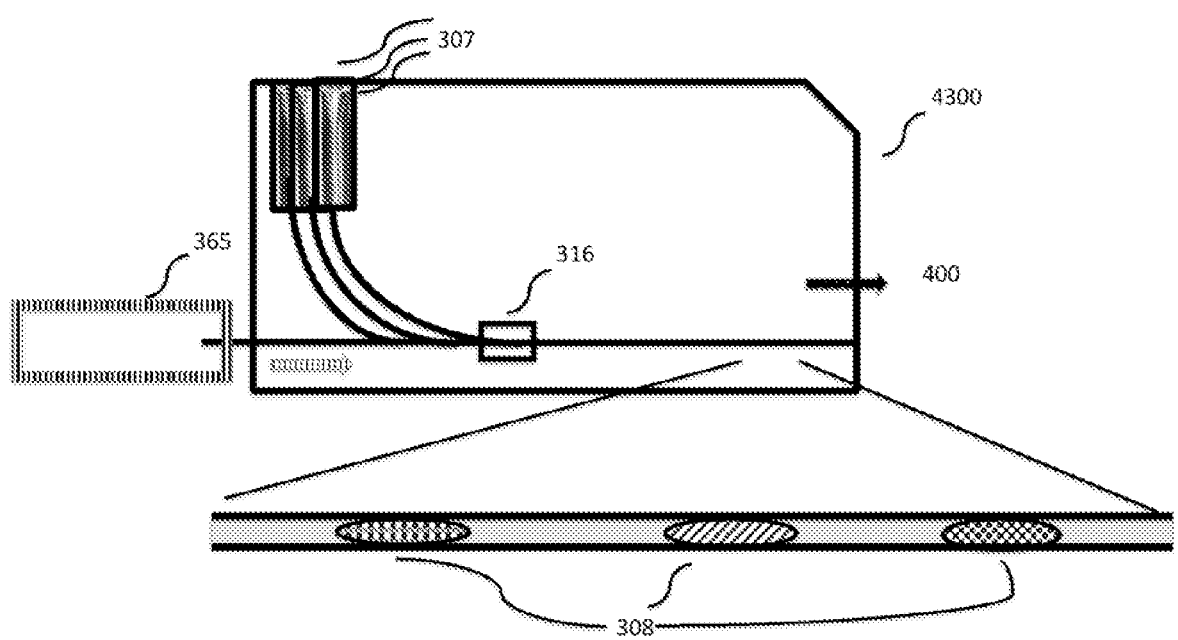
FIG. 6 shows entraining nuclei boluses in a flow system.
Figure 7:
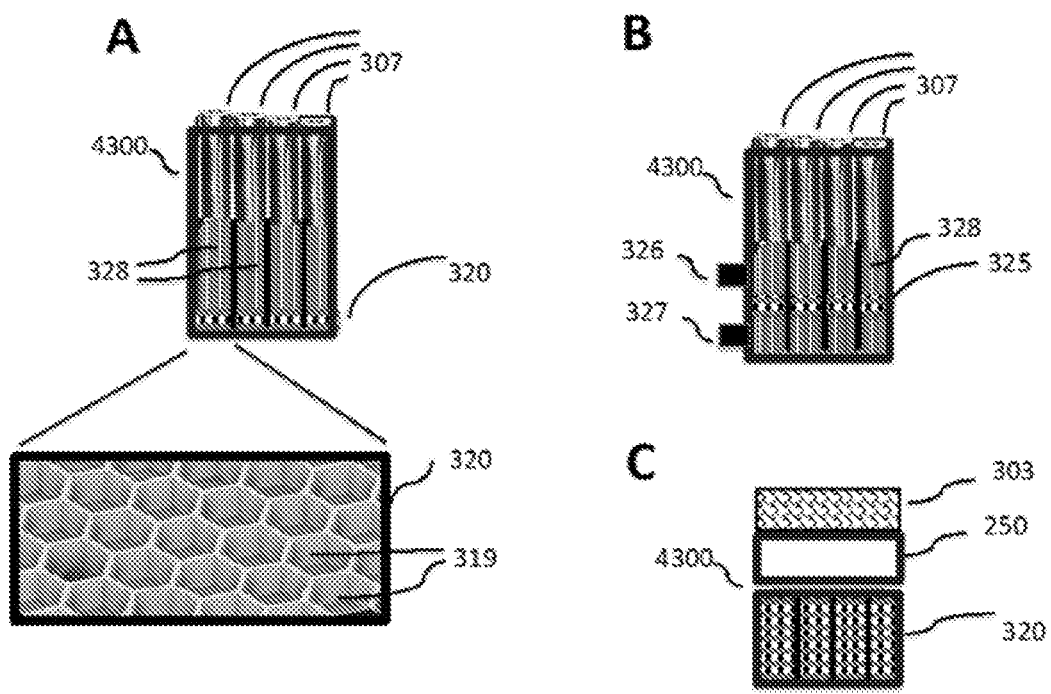
FIG. 7 illustrates three embodiments of a spatial sampler cartridge delivering the boluses (A) to nanowells through the lower array of conduits, (B) to an array of wells designed to caprture individual nuclei or cells, and (C) directly to an array of nanowells.

Referring to FIG. 6 in one embodiment, cartridge 4300 contains the lower array of conduits 307 as an array of capillaries 328. In another embodiment, below array of conduits 307 is an array of nanowells 320 as shown in FIG. 7.

The multifunctional head 330 then delivers nuclei isolation solution 910 from the upper array of conduits 306 through a changeable liquid permeable membrane (not shown) to the tissue section held on the cartridge 4300. The nuclei isolation solution 910 (e.g., 10 mM TrisHCl, 25 mM KCl, 250 mM sucrose, 5 mM $MgCl_2$, 0.1% NonIdent P-40) or other formulations disrupt cellular membranes to generate nuclei as the tissue is simultaneously forced through the 30 micron mesh filter and into a carrier with an lower array of conduits 307 connecting to capillaries or other channels geometrically matching the upper array of consuits 306 or to an array of nanowells 320 on the bottom of the cartridge 4000. If needed, the nuclei isolation solution 910 can be forcibly moved up and down to fluidically disaggregate the cryosection 303, the concentration of detergent increased, or the contact time lengthened before higher pressure is applied. Physical features to disrupt the tissue can be used.

In one embodiment, this method will produce a bolus of 30 micron strained nuclei in suspension in the nuclei isolation solution 910 from each individual microregion 304, for example, 150 micron diameter and 5 to 50 micron deep. Each capillary or nanowell collects only one microregion 304 per tissue slice. Depending on the size of the conduits, or capillaries, these microregions 304 may contain a few or tens of cells, all from the same physical location, all sharing the same microenvironment.

As shown in FIG. 6 for a microflow approach, cartridge 4300 contains the lower array of conduits 307 which is an array of capillaries 318 made with different lengths connecting at a valve such as FROLC valve which can join multiple flows. (See, e.g., U.S. Pat. No. 7,244,961.) Because the capillaries have different lengths, a series of boluses 308 at controlled intervals in a single flow stream can be produced. A flush of the flow stream with an immiscible fluid followed by flow from the multifunctional head upper array of conduits 306 will produce boluses 308 in flow stream. Each capillary can feed individual nanodroplet generators with a single 'spatial' barcode to generate spatially defined microsamples from tissue for output into the Spatial Encoder module 400. After cleaning, a new section can be loaded and the same region of interest can be sampled and barcodes tied to the next 3D layer can be added to reconstruct a 3D representation by sections.

In another embodiment, as shown in FIG. 7A, cartridge 4300 contains the lower array of conduits 307 which separately enter individual chambers 328 which may each contain an array of nanowells 320; the array, 320, of nanowells, 319 can include spatial barcodes attached to the walls with DNA primers. One alternate embodiment uses oligo-encoded nanowells that may be arranged in larger chambers. Ninety-six microregions could be processed in 96 separate individual chambers 328 each with a array of nanowells 320 to isolate single nuclei. In another embodiment, beads containing spatial barcodes could be added during manufacturing and the spatial barcodes interrogated to readout the spatial barcodes.

In another embodiment, as shown in FIG. 7B, cartridge 4300 contains the lower array of conduits 307 which separate enter individual chambers 328 which each contain an array of holes 325 mounted in the middle of individual chambers 328. The array of holes 325 can be an array of capillaries 318 or may be injection molded with opening that may be 30 microns in diameter, or larger, or smaller. By positioning the array of holes 325 above the bottom of individual chambers 328, single cells or nuclei can be trapped on the array of holes 325 and reaction mixtures added directly to the array of holes 325 to perform chemical or biochemical reactions. The individual chambers can have optional fluidic input 326 and fluidic output 327 to allow reactants or buffers to be added.

In another embodiment, as shown in FIG. 7C, cartridge 4300 has the array of nanowells 320 directly integrated into the cartridge replacing the lower array of conduits 307.

In another embodiment, to produce single cells, the upper array of conduits 306 delivers a tissue specific dissociation formulation to specimen 301 which can be a cryopreserved tissue 303 and after an incubation, the dissociated cells from microregions 304 are delivered to the Spatial Encoder 400 for flowthrough or nanowell processing.

Figure 8:
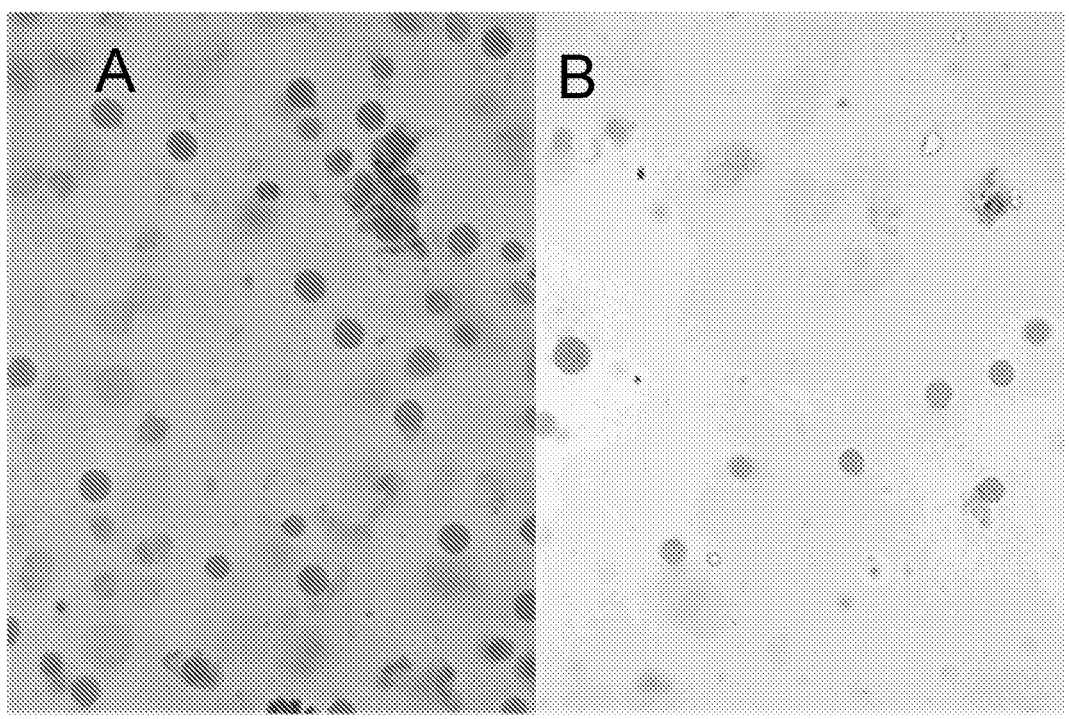
FIG. 8A shows a production of nuclei from flash frozen mouse kidney with incubation in nuclei isolation solution with no mechanical agitation and FIG. 8B shows the production of nuclei from flash frozen mouse with incubation in nuclei isolation solution after three times passage through 75 μm stainless steel mesh.

FIG. 8A shows results of processing flash frozen mouse liver that had been finely manually sectioned and incubated with nuclei dissolution solution 920 produced nuclei at room temperature with no mechanical processing. The finely sectioned flash frozen liver had a nuclei isolation solution 920 added and then after seven minutes a sample was taken, and ten µl of the sample was mixed with ten µl of Trypan blue, loaded onto a disposable hemocytometer, and visualized on a brightfield microscope. This result is proof-of-concept of producing nuclei from thin slices of frozen tissue with no mechanical disruption. FIG. 8B shows the results of processing 1 mg frozen slice of liver with nuclei dissolution solution 920 that has been fluidically driven through a 75 µm stainless steel mesh 250 three times and then visualized and counted on a hemocytometer: the 1 mg frozen slice produced well defined nuclei after passage through the mesh.

Figure 9:
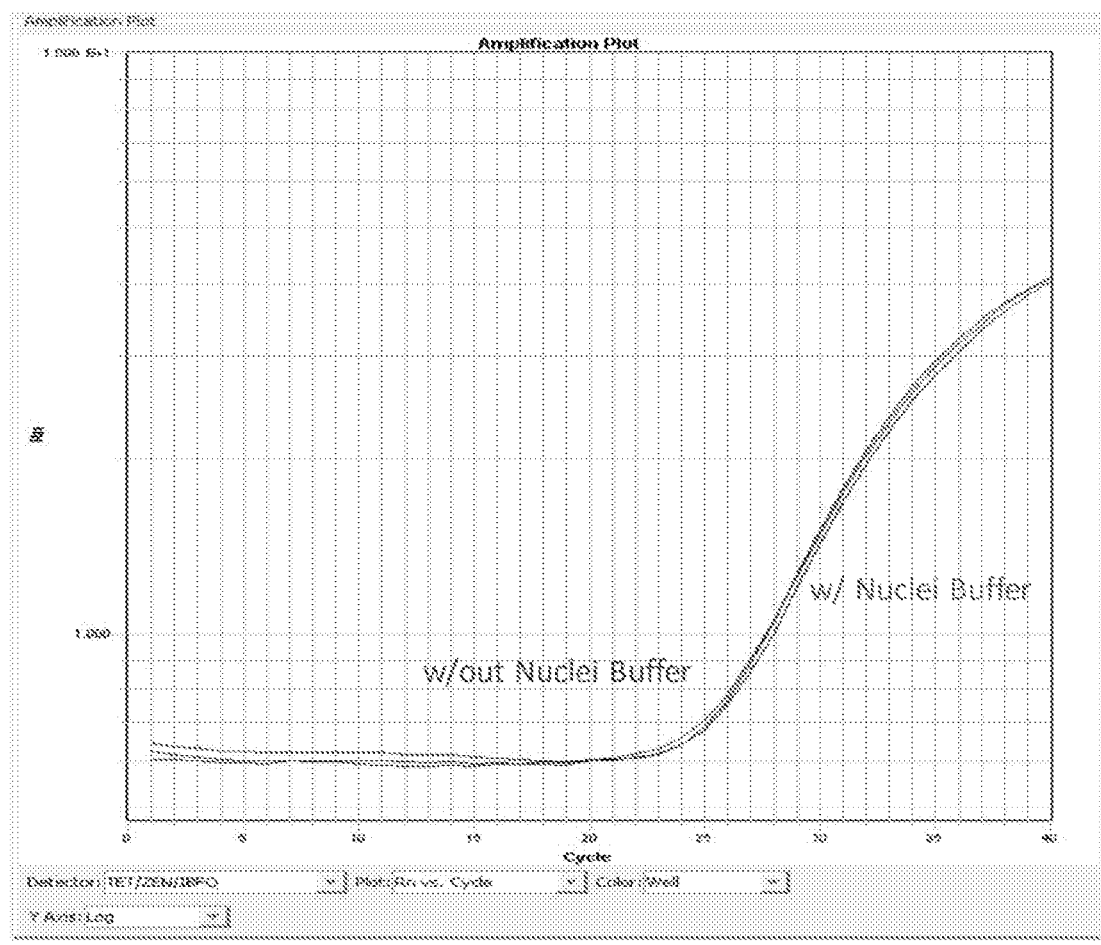
FIG. 9 shows nuclei isolation solution does not inhibit RT-qPCR. 1 μL of total RNA from mouse spleen cells and 3.5 μL of nuclei isolation solution or water was added to 5.5 μL of OneStep RT-qPCR master mix with actB primers designed for transcripts, and thermocycled.

To test if the nuclei isolation solution 910 impacted downstream nucleic acid enzymology, mouse spleen RNA was processed by RT-qPCR (qScript XLT One-Step RT-qPCR ToughMix Rox, QuantaBio) with or without undiluted nuclei isolation solution. FIG. 9 shows neither the reverse transcriptase nor the DNA polymerase were inhibited by the nuclei isolation solution, suggesting it will not inhibit downstream molecular biology, possibly obviating the need to change buffers and simplifying the workflow.

Extensive quality control (QC) assays can be carried out to quantify performance in singulating nuclei as metrics to assess and tune the module development. Quality control assays for tissue into cells and nuclei dissociation for titer and viability can use an automated cell counter, such as the Countess II FL (Thermo Fisher) or microscopy, as well as RT-qPCR for the actB housekeeping gene and fos, a stress induced gene. For RNA quality, after cDNA production, the size distribution can be measured (Bioanalyzer, Agilent) and qPCR performed on housekeeping and key marker genes from specific cell types to determine RNA integrity. RT-qPCR assays can have ERCC spike-in controls and additional controls for processing steps including additional spiked in controls, with for example, different barcodes or mass tags, for each processing step. These controls can be used to tune processing parameters. NGS can also be used, for example cDNA libraries can be constructed using micronozzles, and after library preparation, scRNA-Seq carried out on Illumina or other instrumentation. Gene coverage analysis can reveal the percent of full length cDNA recovered and any excess coverage at the 3'-end of genes indicating the harshness of tissue processing methods.

A very low throughput embodiment can produce microregions from frozen tissue. Two machined mating holders each that has a single 100 micron/188 micron OD capillary, and 'eggcrate' 377 adapters to hold the capillary can be made with lower one fixed and in one embodiment chilled by a Peltier. The upper one can be held on a micromanipulator 3-axis stage, engaged at the top with the upper capillary attached a syringe pump at the other end.

Tissue can be placed in the carrier and the upper holder lowered to define a single microregion. The syringe pump can then deliver nuclei isolation solution 920 through the upper capillary to the tissue and a microregion 304 can be collected, such as into a single microfuge tube for RT-qPCR analysis or for bulk and single nuclei sequencing. Multiple microregions 304 can be pooled for processing or the size of the microregion changed. The scale can be increased to 12 and then 24 microregions in parallel with the Spatial Encoder 400 developed to multiplex 12 barcodes.

Different mouse or rat tissues can be tested to measure the variability from tissue to tissue for flash frozen tissue; for fresh tissues, little variability has been observed from tissue to tissue for production of nuclei for soft tissues, while large variations exist for the production of single cells (unpublished observations).

Leakage can be resolved with gasket and cartridge design; note leakage between microregions will not overly confound the data analysis. Speed of production can be adjusted with detergent concentration, temperature, and added mechanical forces. Cell debris, and ambient nucleic acids can also lower the performance and quality metrics of the resulting NGS data and may require additional processing such as removal by in-line tangential flow filtration. The design of the carrier and the workflow (time of exposure, temperature, pressure, detergent and additive concentrations) can be iterated to improve performance. Alternative methods of microscale punching of microregions into microtubes, pick-and-place robotics to move produced microregions into microtiter plates, and incorporating labels in the can be employed.

The hardware, electronics, chemistry, cartridge, and software of the Spatial Sampler module are described. The software can use LabScript™ software (McIntosh Analytical to control motors through boards and temperature using Peltiers or other devices comprising resistive heaters, chillers, or others. Three OEM stages can be used to move the section carrier and multifunctional head and affixed to an instrument chassis. The specified positional accuracy can be 2 micron with travel of 10 cm for two axes and <1 cm for the third (Z). The stages can be controlled by LabScript software with scripts written for the needed motions or other software. In one embodiment, the multifunctional head can have an array of capillaries 318 that inject nuclei isolation solution 920 at 24 to 96 injection points from the array on the multifunction head through the tissue on the carrier. A 3D printed multifunctional head can be held by the three axis robot through a support that will also bring the fluidics 339 from syringe pumps to the upper array of capillaries in the multifunctional head.

For the microflow approach, the upper holder can, as needed, pick up a disposable liquid permeable membrane to minimize contamination. The carrier would be as simple as a supported mesh or could include the 'eggcrate' 377 and a bottom alignment feature to dock with the lower array.

A Spatial Sampler module can have an 1, 12, 24, 96, 384 or other channel array head. A cleaning cycle can be developed, with 100 mM NaOH, followed by a buffer rinse, and airflow to dry the capillaries or other methods. Contamination of the reusable components can be measured by alternating species and assaying with qPCR and sequencing. The Spatial Sampler module can be scaled up to 96 capillaries and to 384 or more.

Flowthrough Spatial Encoding of Microregions from Frozen Tissue.

The microflow Spatial Encoder module 400 inputs ordered single nuclei from microregions from the Spatial Sampler module 300 and encodes the spatial origin of the nuclei into DNA for ssnRNA-Seq. This is done by adding beads with known barcodes (or mass tags for proteomics) to each bolus to correlate with the original spatial information as nanodroplets are made.

For ssnRNA-Seq, the cells are lysed and the mRNA 681 hybridized 682 and reverse transcribed 683 to encode the spatial information as a barcode in the cDNA 684. The cDNA now contains spatial, cellular, and molecular barcodes in addition to any sequencing and amplification primers, i.e., T7, PCR. The samples can be pooled for library preparation and analysis for NGS sequencing.

One embodiment of the hardware, beads, and workflows to introduce single nuclei or single cells and process them into nanodroplets 325 or surfaces to encode spatial position is described. For a large part of the workflow, single to 8 to 96 micronozzle systems are available. A brute force production system could mate the 96 capillaries from the Spatial Sampler module to a Telos System (Dolomite) with 96 nozzles using 12 chips, each with 8 micronozzles.

Figure 10:
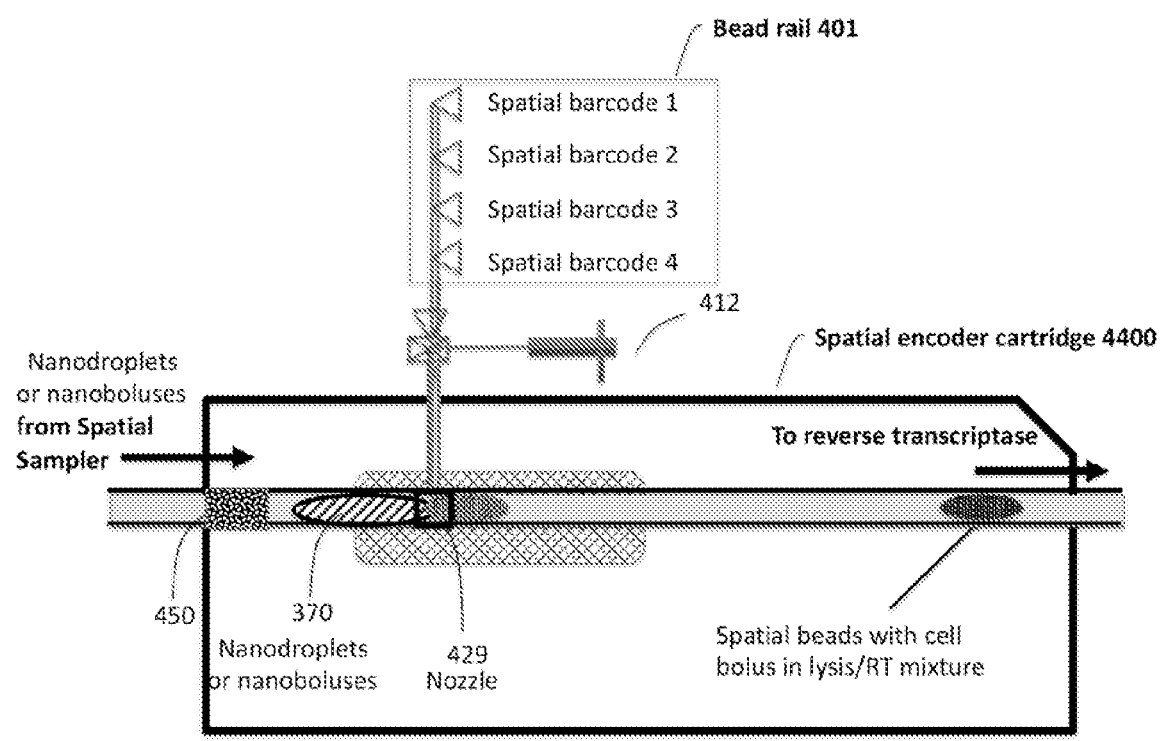
FIG. 10 shows a schematic of Spatial Encoder module fluidics showing a reagent rail with four barcodes.

As shown in FIG. 10, in one embodiment the Spatial Encoder cartridge 4400 can introduce spatial barcodes on the beads into nozzle 429 to produce cell or nuclei nanodroplets 325 in lysis/RT mixture, with all or most of the cells or nuclei having a bead with a spatial barcode. Detection region 450 can be interrogated to detect bolus 308 as it approachs noozle 429 to place beads with spatial barcodes in proper position to merge with individual boluses 308.

If Spatial Encoder cartridge 4400 connects to 12 spatial barcodes, then only one cartridge of 8 micronozzles is needed to tag 96 microregions 304. The spatial barcode can include additional indexes to identity each nozzle for 2D reconstruction and for each layer or section number for 3D reconstruction. This approach is very scaleable. An issue is the delivery of the 12 spatially encoded bead sets into the fluidic stream and into the 'bead feed' at the proper timing and changing the beads on demand. This can be addressed by adjusting the gap between boluses of microregions in the Spatial Sampler module and by detecting boluses with an optical sensor or imager to trigger the proper bead batch. The gaps can be made very long or short as needed.

Figure 11:
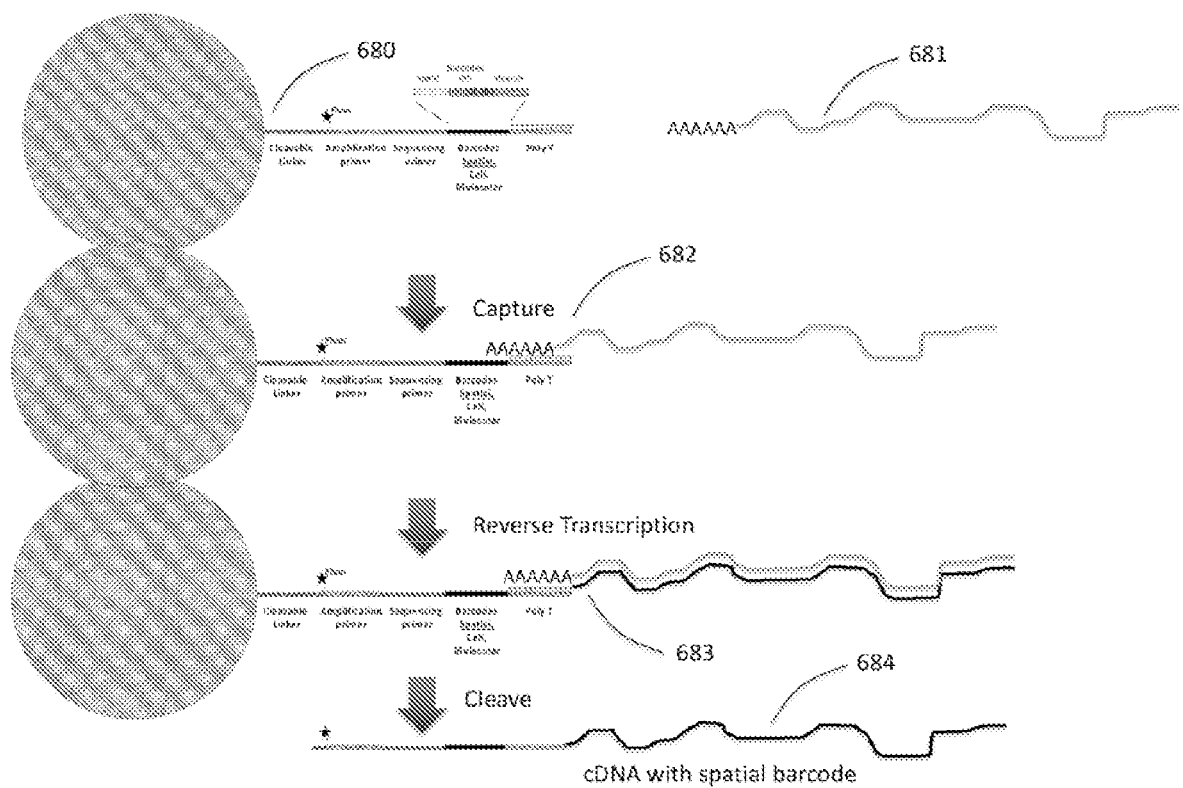
FIG. 11 shows a high level process design for beads encoding spatial information.

As shown in FIG. 11, for ssnRNA-Seq, oligonucleotide-functionalized beads or nanowells can have a poly T sequence to capture polyadenylated mRNA. The oligos will be barcoded for spatial information (by the lot of each set of barcodes and the sample they were added with) as well as cell and molecule identification and amplification and sequencing primer sequences.

Oligonucleotides can be designed to provide 1,024 barcodes with 5 bases of spatial barcodes for spatial resolution (including layer) and QC barcodes. Cell barcodes can be 6 nucleotides that are synthesized by split-pool and UMIs can be 8 nucleotides by degenerate synthesis; the cell barcodes only need to identify within a microsample/bolus (the spatial barcode discriminates against all cells outside the microregion). The oligos, such as amino-modified oligonucleotides, will be initially attached to commercially available paramagnetic beads or nanowells by covalent crosslinking or biotin. The oligo sequence can be evaluated for proper functioning and additional spacers added as needed to minimize bead/surface reaction interferences.

In one embodiment, the hardware and software must deliver beads with a unique, known, spatial barcode to each microsample in the flowthrough approach. The fluidic delivery will use a reagent rail to access beads each with a single spatial barcode as shown in FIG. 10. This fluidic approach could scale to 1,000 spatial barcodes per run and eventually microfluidic chips could be used to deliver the beads.

In one embodiment, micronozzle chips (Dolomite) can be used with Fluoridrop emulsion phase (Dolomite) with three syringe pumps under LabScript software control as the core of the Spatial Encoder module 400. One pump can drive solutions of beads with oligos, a second pump can drive nuclei suspensions, and a third can drive the emulsion oil. The flow rates can be adjusted using a microscope to produce steady streams of droplets; stirring may be required depending on bead composition. An optical sensor 450 can be incorporated upstream of the micronozzle to trigger changing spatial barcodes.

In one embodiment, single channel fluidics can be used to demonstrate the workflow, i.e., inputting a bolus 308 of nuclei or single cells in a microfluidic flow and encoding the original spatial relationship using four DNA barcodes on oligonucleotides attached to beads (shown conceptually in FIG. 10). A stream of beads with one spatial code in lysis/RT mix can be added to the bolus of nuclei from a microregion. Monodisperse nanodroplets from single nuclei with spatially coded beads with lysis/RT mix can be produced As needed, the geometry and flow rates can be altered to adjust bolus size and flow rates with a goal of a Poisson distribution of single cells with each nanodroplet having a bead. Adding different mass tags to single cells or antibodies with DNA barcodes to encode spatial position can be performed to enable additional encoding modalities.

The ability to add two different sets of beads (or initially fluorescent beads) to alternating samples can determine the needed accuracy in timing and volumes and to decide if optical detection of the cell bolus is needed. This can be directly scaled up to two micronozzles for the 24 microsample scale.

The process can be developed with rat liver nuclei to develop the process and then progress to alternating boluses of mouse and rat to detect contamination and inform system cleaning development. After lysis, the RTase reaction can either be performed in nanodroplets, or after breaking droplets: both methods will be tested. The RTase conditions can be optimized with mRNA standard for bulk reactions, and then for nanodroplets. The system can add spatial DNA barcodes or mass tags to existing nanodrop generators. The RTase reaction products can be assayed by qPCR and by processing into libraries with QC steps. External polyadenylated transcripts 250-2,000 nt in length at a $10^6$ range of concentrations can be used to assess the dynamic range and range of detection with NGS analysis (ERCC RNA Spike in Controls, 4456740, Life Technology). Encapsulation of nuclei with agarose at the formation of nanodroplets will be tested to determine if multiple reactions in a row are possible.

b. Spatial Encoder.

The Single Cell Spatial Analysis System Spatial Encoder module 400 inputs the ordered microsamples which may contain single cells or groups of cells from the Spatial Sampler module 300 using the Spatial Sampler output such as an output microchannel as an input to the Spatial Encoder module 400. The spatial encoder subsystem can place the microsamples in a sequential ordered arrangement in a fluidic stream. This sequential arrangement is referred to as a train, and microsamples in a train are said to be entrained. In a preferred embodiment for nucleic acid encoding, adds beads with known barcodes to correlate with the original spatial information into boluses, creates microdrops, (nanodroplets in some implementations, or boluses in other implementations), preferably with one or less cells per nanodroplet. A bolus 308 is typically elongate in shape, while a nandroplet is typically spherical. A bolus typically has a volume of at least 3 microliters. A nanodrop typically has a volume of no more than 3 microliters, e.g., about 1.5 microliters. In a preferred embodiment, the Spatial Encoder module 400 outputs single cells or nuclei in nanodroplets or boluses with spatial barcodes on beads.

One embodiment of spatial barcoding is to use beads with oligonucleotides with spatial barcodes 680 is illustrated in FIG. 11. The beads with oligonucleotides with spatial barcodes 680 can be paramagnetic beads, agarose beads, or others, and have surface chemistry optimized for the nucleic acid capture and subsequent chemistries. The term beads is also used to refer at times to patterning the oligonucleotides with spatial barcodes on a surface rather than on a bead.

Oligonucleotides with spatial barcodes can be generated by synthesis using standard commercially available phosphoramide or other technology. In one embodiment, the oligonucleotide has a cleavable linker, attached to an amplification primer with fluorescent label, a sequencing primer, barcode region, and capture region. The barcode region is comprised of a spatial barcode, cellular barcode, and molecular barcode.

In one embodiment the spatial barcode can be 5 nucleotides long to provide 1,024 barcodes for spatial resolution. Cellular barcodes can be 6 nucleotides, or other lengths, and synthesized by split-pool synthesis, and molecular barcode can be 8 nucleotides synthesized by degenerate synthesis; the cellular barcodes only need to identify cells from within a single microsample since each microsample is encoded with a spatial barcode. In a preferred embodiment, each spatial barcode is unique for each set of microsamples that are analyzed together. In other embodiments, spatial barcodes can be shared between microsamples and then resolved bioinformatically using cellular barcode to sort and cluster by cells to resolve spatial barcode ambiguities. Spatial, cellular, and molecular barcodes can be of different lengths or in different orders, or dispersed among other elements of the oligonucleotide with spatial barcode 50 without limitation.

The oligonucleotides, such as amino-modified oligonucleotides, can be initially attached to commercially available paramagnetic beads by covalent crosslinking and may include a cleavable linker bond (Ju. J. et. al. U.S. Pat. No. 9,133,511. Sep. 15, 2015.), (Knapp D. C. et. al. Bioconjug Chem. 2010; 21(6):1043-55.), (www.clickchemistrytools.com/products/click_chemistry_toolbox), (Olejnik J. et. al. Nucleic Acids Res. 1996; 24(2):361-6.). Fluorescent probes can be attached to the oligonucleotide distal from the bead and cleavable bond or alternatively fluorescent nucleic acid base analogs can be used such as 2-Aminopurine (Wilhelmsson, Quarterley Reviews of Biophysics, 43, 2, 2010, 159-183). The cleavage of labeled oligonucleotides can be used for assay development since the oligonucleotide can be analyzed by fragment sizing on CE with the fluorescent tag to give the distribution of sizes to assess library quality.

The hardware and software of the Spatial Encoder module 300 must deliver a set of beads with a unique, known, spatial barcode to each microsample. Referring to FIG. 10, the Spatial Encoding fluidic delivery can use a spatial barcode reagent rail 401 to access beads each with a single spatial barcode, controlled by spatial barcode reagent rail valves respectively, to deliver reagents through by spatial barcode fluidic channel to spatial barcode syringe pump 412. It is within the scope that the spatially barcoded beads will scale to 1,024 or greater number of spatial barcodes per run for the Single Cell Spatial Analysis System.

As microsamples 370 are moved from Spatial Sampler output, such as a microchannel, reagent rail syringe pump 412 and spatial barcode reagent rail 401 can select a reagent of singly spatially barcoded beads, such as beads all with a single spatial barcode, but with unique cellular barcodes and UMIs, and delivers a bolus of beads through spatial barcode connecting channel to spatial encoder junction to merge with the microsample 370 in spatial encoder cartridge 4400. Optical, conductance, or other sensors can be incorporated as needed to detect the microsample 370 in the bolus and coordinate the addition of the spatially barcoded beads to the bolus.

The bolus then passes through a spatial encoder microchannel to nozzle 429 where an immiscible fluid such as Fluorinert, Droplet Generation Oil (Biorad, #1863005), or other solutions can be added by nanodroplet generation syringe pumps to the bolus to produce nanodroplets, preferrably 1.5 nL, and sent down spatial encoder output microchannel as output from the Spatial Encoder. Nanodroplet generation syringe pumps can also be combined into one syringe pump that has two microchannels that split in two from nanodroplet generation syringe pump output to join the microsample 370 with barcoded bead bolus from either side to produce nanodroplets, eliminating the need for a second nanodroplet generation syringe pump. Nozzle designs and circuits are incorporated by reference (Macosko E. Z. et. al. Cell. 2015; 161(5):1202-14.) (Klein A. M. et. al. Cell. 2015; 161(5):1187-201.) (Geng T. et. al. Anal Chem. 2014; 86(1):703-12).

In an alternative embodiment, the microsample bolus with the added spatially barcoded beads are processed as a bolus without the formation of nanodroplets. In this approach, the bolus may be preferably less than 5 nL, or 10 nL, or 25 nL, or 100 nL, or 250 nL, and 10,000 microsamples may be less than 2.5 mL.

In one embodiment, single channel fluidics are used. For example, 100 nL of beads with one spatial code are added in junction to the, for example, 100 nL of microsample in output microchannel and lysis and/or reaction mixtures, such as lysis/reverse transcriptase mix, added separately through spatial encoder reagent syringe pump and reagent connecting microchannel.

Monodispersed nanodroplets from single cells with spatially coded beads with lysis and/or reaction mixtures, e.g., lysis/RT mix for RNA-Seq, lysis/restriction mix for DNA sequencing, are then be produced using a nozzle 429 (Macosko E. Z. et. al. Cell. 2015; 161(5):1202-14.) (Klein A. M. et. al. Cell. 2015; 161(5):1187-201.) (Geng T. et. al. Anal Chem. 2014, 86(1):703-12.) and output through spatial encoder output microchannel 430. As needed, the geometry and flow rates can be altered to adjust size and flow rates to produce a Poisson distribution of single cells with each nanodroplet preferably having a spatially barcoded bead.

In other embodiments, the bolus from the Spatial Sampler module 300 is physically separated by structures, volumes, or surfaces, for example, by placing the bolus into a microtiter or smaller well or tube. The Spatial Sampler module 300 output can be used to be physically dispersed onto the surface of a material comprised of agar, membranes, arrays of beads, microscope slides, flow cells, and others. The physical dispersion can be by moving the surface under a capillary or other flow, by printing with a microarray pen, by piezospraying, electrowetting, microfluidics, or other methods. The physically separated microsample bolus can be dispersed such that, for example on the surface of agar, all cells are far enough apart to be processed as single cells.

In one embodiment, a spatial encoder reagent syringe pump adds a low melting temperature agarose to encapsule the nanodroplet with heated liquified agarose (Geng T. et. al. Anal Chem. 2014; 86(1):703-12.) during the formation of nanodroplets. Once cooled, the agarose can be used as a barrier permeable to low molecular weight components, such as reaction components, but not to high molecular weight components such as nucleic acids when it is cooled. The use of agarose to encapsulate the reactions enables multiple sequential reactions or manipulations in a row to be performed in the nanodroplet 325 with reactants diffusing into the agarose encapsulated nanodroplet.

Example 1: Nanowell Processing Spatial Encoding of Microregions from Frozen Tissue In an alternative approach the Spatial Sampler module 300 can output nuclei into spatially barcoded nanowells 319 as illustrated in FIG. 7 or beads with the spatial barcodes can be added to an array of nanowells 320 that does not have spatial barcodes attached to the nanowells.

The specimen 301 can be held in the same carrier for processing but in this approach the output from the capillaries is directly to nanowells. The nanowells 308 on the bottom of the 24 or 96 reservoirs can be of the order of 30 micron diameter to only accept one nucleus and oligonucleotide primers with poly-T, and spatial, cellular, and UMI barcodes and amplification primers attached to the walls of the wells. Devices for the nanowell 308 approach can be prototyped using 3D printing, embossing, and glass etching. The nanowells 308 can also be coated with anti-nuclear antigens, e.g., NeuN, for capture of neuronal nuclei. The nanowells 308 can replace the downstream nanodrop generation and potentially simplify the system as well being adaptable to more assays than nanodrops.

Example 2: Systems Integration of a Low Throughput Spatial Sequencer to Process Solid Tissue in Spatial Single Nuclei, Ready for Downstream Sequencing A low throughput platform is described that integrates the Spatial Sampler 300 and Spatial Encoder 400 workflows together and with the downstream NGS workflows. As individual components, workflows, and modules are developed they can be manually integrated and then automated using LabScript software for instrument and component control using electronics and firmware for the single-cell sequencing infrastructure.

The integrated workflow can developed first on the bench with can cells or nuclei from fresh or flash frozen rodent tissue. Nuclei produced from the Singulator prototype will be processed into single nuclei or bulk libraries on a micronozzle (Dolomite) at a range from 10 to 1,000,000 nuclei. The nuclei can be assessed by qPCR and the libraries will by qPCR (Kapa, Library Quant Kit for Illumina Sequencing Platforms) and by length distribution (Bioanalyzer). As appropriate, the libraries can be sequenced and the single nuclei compared with bulk representation. Microregions 308 can be tested for sensitivity and cellular representation to determine system workflow options. The amount of nuclei purification required can be tested with NGS and strategies to improve performance, such as pull-down of nuclei or tangential flow filtration can be employed.

The workflow can be developed on the system as each module is brought up. First single microregions 308 from rat liver can be processed and integrated to a single micronozzle 429 and standard beads. The requirements to pool samples can be tested. As described above the system can scale from 1 to 12 to 96 or more.

The downstream NGS workflow can use single-nuclei sequencing for NGS sequencing with a RNA-Seq computational pipeline to assess the quality of the data and, optionally, the reads trimmed and those with poor quality filtered out. High quality reads can aligned to reference genomes or transcriptomes using one of the many available high-throughput sequencing mapping tools. Alignments can be assembled into full-length transcripts based on a reference genome and subsequently passed to quantification tools to obtain a measure of expression. After completing these main steps, several differential analyses can be executed to identify differentially expressed genes and transcripts.

Example 3: A High Throughput Spatial System with Imaging and Additional Applications to Process Frozen Tissue Sections to Spatially Analyzed Data The Spatial Sequencer 100 can be scaled up to provide multiplexed, high-throughput, high resolution mapping of human tissues, integrated imaging, and multiple 'omic applications. The platform can be designed to be extensible for many biomolecules. Multiple additional human tissues can be mapped at the single cell resolution to provide an invaluable tool to understand cellular microenvironments and tissue organization.

In one embodiment, the Spatial Sequencer 100 can be a high throughput system that can image the section, optionally apply contrast agents, and repeatedly sample a larger format tissue sections to rapidly generate spatially encoded samples for multiple genomic and proteomic assays. Building on the basic design of the low throughput system, the number of microregions processed can be scaled from 24 to 96 or 384 and the micronozzles increased to 8 with increased multiplexing. The ability to map multiple auto-feed sections as a 3D representation can be added.

Example 4: Development of Optics and Hardware Capabilities

Imaging tissue section is critical to determine pathology and direct analytical efforts to regions of interest. A high-resolution imaging station can be added or integrated with and potentially lower resolution imaging incorporated on the multifunctional head. The capability to deposit fluids such as contrast agents onto the tissue section can be added with multiple piezoelectric nozzles receiving different solutions.

To integrate an imaging station or capability, commercial products can be used to scan at cellular resolution such as a modularly constructed imager which permits choice of blue, green or near IR optical heads and cellular resolution as a possible station and the information from the scan used to identify regions of interest.

In an alternate embodiment, an epifluorescent imager can be designed with illumination by a green or red laser diode through a beam-splitter with detection by a >10 megapixel CCD/CMOS detector after blocking the laser line and focusing. The optical can will be developed and refined in a ray tracing program for commercially available lenses and filters in a glue-up fixture. The components can installed and aligned on an optical bench, and the response of the camera (or COTS device) to different levels of illumination characterized. The output of the imaging device can be processed in LabScript or other software to quantify total number of cells and non-viable cells. Camera control and image acquisition can be based on Point Grey/FLIR Spinnaker SDK optimized for machine vision applications or other libraries for spectral analysis and cellular analysis. Examples of image processing using Image J freeware, Cell Profiler, or other software can be compared for parameters known to impact cell recognition.

Example 5: Spatial Proteomic Applications

The Spatial Sequencer 100 platform can enable multiple proteomic assays. Mass tags or other metabolomic or proteomic labels can be added at multiple points in the workflow: in the Spatial Sampler module 300 or in the spatial encoder module 400 instead of by a bead or by a nanowell. A bottom array portion of the cartridge can have unique mass tags that are solubilized as nuclei or single cells are liberated. The mass tags can then either be entrained with the bolus or are deposited with the bolus into nanowell plates. Upon analysis, the MS readout of the mass tags decodse the microregion where the nuclei or the released cellular cytoplasm originated.

In many applications, antibodies are labeled with DNA barcodes to measure antibody-epitope interactions, now by NGS If the antibodies are to specific nucleus membrane components (or for cells to cell surface epitopes), have spatial barcodes attached, and are mixed in upon cellular lysis, only nuclei or cells with the epitopes will be captured. The nuclei or cells can be washed and then lysed and the spatial barcodes readout by NGS to quantify binding by specific cell types for example.

Example 6: Spatial Single Nucleus Chromatin Accessibility Assay

In the ATAC-Seq application, a Tn5 transposon with sequencing adapters 'hops' into regions of the chromosome that are opened up to address regulatory variation. In one embodiment, the Tn5 transposon is modified to have spatial barcodes and the polyT beads replaced with Tn5 transposons with spatial addresses. The protocol can also be readily adapted to the nanowells embodiment with pooling after the hop. ATAC-Seq from bulk measurements can be compared with aggregating ssnATAC-Seq.

Example 7: Spatial Single Nuclei DNA Sequencing

The Spatial Sequencer 100 enables multiple approaches to be tested for spatial single nuclei DNA sequencing. In one embodiment microregions 304 are collected in nanowells, with Phi 29 amplification of the DNA, and the workflow done conventionally after directing the microregions 304 into individual reactors with different spatial barcodes.

In another embodiment, low melting point agarose is employed as a heated liquid to encapsulate single nuclei so that low molecule weight reactants, such as nucleotides and enzymes, can be exchanged through the gel surrounding the nanodroplets 325 after cooling. Nuclei can be passed through the micronozzle with low melting point agarose with biochemicals to form 'nuclei beads' in an emulsion with spatial oligos complementary to targeted sequence of interest. The beads can be treated in multi-steps off the instrument to perform multiple reactions in a row, much like nanoreactors. The beads can re-form on chilling, can be collected and the next reaction added. In one embodiment, a dsDNA Fragmentase® (NEB) step can be performed followed by heating and then snap chilling to form single stranded regions. The DNA can be hybridized with the spatially barcoded targets and, after reagent change through the gel bead, PCR amplified in the nanoreactors with the appropriate primers.

Example 8: Spatial Methylation Application

Both the nanowell approach and the low melting point agarose with nanodroplets 325 can be used to determine the methylome. For low melting point agarose with beads, the approach would be to isolate the single nuclei in nanodroplets 325 containing beads with targeted oligos with spatial codes, lyse, and collect the beads. The beads are treated with bisulfite. Beads are chilled and collected, and after reagent change through the solidified agarose surrounding the nanodroplet with bead, the PCR amplified in the nanoreactors with the appropriate tagged primers.

Example 9: Tissue Expansion for Spatial Sequencing

The expansion technology of Boyden can allow conversion of frozen tissue by four-fold, and reducing the number of nuclei in the microregion. Experiments can be performed to see if frozen tissue can be expanded and if so if nuclei can be released. This can allow one size or array head to collect both microregions with 10s of nuclei and single nuclei by using expansion.

Example 10: Spatial Sampling Using Microsyringes

In another embodiment, the spatial sampling to collect microregions is done using a microsyringe instead of the sampling head. In this embodiment, a microsyringe, e.g., Hamilton microsyringes, (1.2 µl, 203185), is controlled by a robotic device to deliver nuclei isolation solution 920 to a microregion 304 on the specimen 301 or cryosection 303, and then to as needed pipette the fluid back and forth over the microregion 304 and then pull the solution from disrupted tissue, now containing nuclei or single cells, into the microsyringe. The microsyringe can be moved by the robotics to the appropriate destination for the next processing steps.

In some embodiments the microregion is moved to a nanowell 319 and processed. In other embodiments the microregion 304 in the micropipette is moved to a Spatial Encoder module 400 and deposited into a reservoir that is then used to create nanodroplets 325 for spatial encoding into the nucleic acid. In some embodiments, the microsyringe can contain the spatial barcodes attached to the microsyringe barrel or plunger, or on beads preloaded, or beads can be picked up for each barcode from a storage container, e.g., a microtiter plate, Eppendorf tube, or other device, and then delivered to a nanodroplet generator.

Example 11: Integrated Spatial Sampler and Spatial Encoder Cartridge

Figure 12:
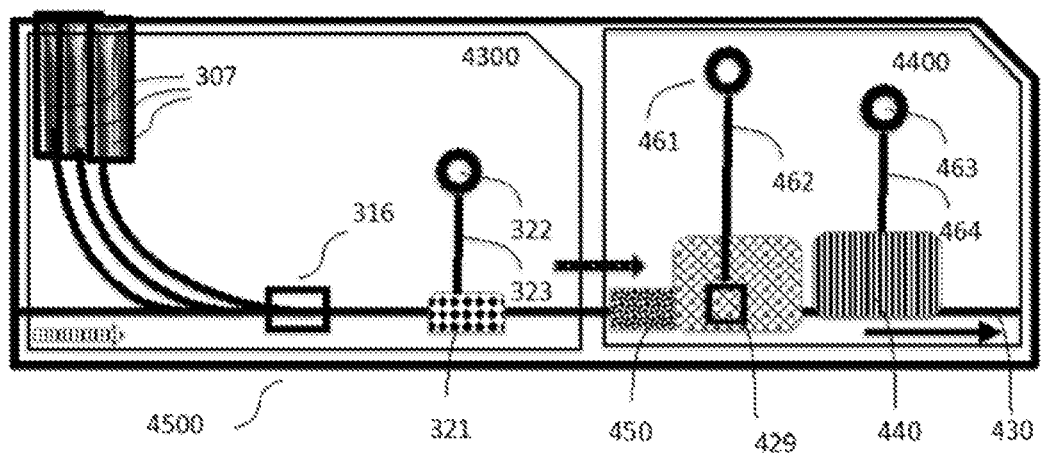
FIG. 12 shows a cartridge that can input microregions and process single cell or nucleus to encode the spatial information at a single or multi-cell level.

In one embodiment, illustrated in FIG. 12, the spatial sampler cartridge 4300 and the spatial encoder cartridge 4400 are combined into a single integrated cartridge 4500. Integrated cartridge 4500 can process single cells or nuclei from specimen 301 after receiving dissociated single cells or nuclei though mesh 250 into lower array of conduits 307 and to FROLC connector 316 to produce single cells or nuclei entrained as a series of boluses 308. Optional sample preparation processor 321 purifies the single cells or nuclei by functionalities such as acoustic focusing, tangential flow filtration, hydrodynamic flow, electrowetting, electric focusing, bead purification, flow cytometry, or other modalities that do not interfer with the order of the boluses; fluidic connection 322 is connected by line 323 to add reagents to sample preparation processor 321. Optional optical interrogation area 450 can have features to reflect, focus, or filter light. In a preferred embodiment nozzle 429 joins channel 462 to fluidic connection 461 which can connect to a spatial barcode reagent rail 401 to add spatially encoded beads. In another embodiment, a nozzle is not used, and the boluses 308 entrained in order have spatial barcode reagent with lysis and reverse transcription added to metagenomics of a microregion 304 or the bolus 308 can have solutions with high viscosities, such as polyethylene glycol or low melt agarose added to slow diffusion between regions of the bolus 308 during the reverse transcription.

In one embodiment, after generation of nanodroplets (which do not touch the side of the conduit) from boluses 308, the nanodroplets 325 can be processed on the cartridge 4500 in reaction chamber 440. Reaction chamber 440 is connected to channel 464 to fluidic connection 463 which can connect to reagents on the instrument, or the reagents can be placed on cartridge 4500. In a preferred embodiment, the temperature of reaction chamber 440 can be adjusted by the instrument to a range from under 4° C. to over 95° C. to perform reactions such as reverse transcription to incorporate the spatial barcodes. In one embodiment, reverse transcription is performed in reaction chamber 440 at 37° C.

In some embodiments, when magnetic beads are used, magnetic fields can be applied by the instrument to reaction chamber 440 to perform a series of reactions after reverse transcription such as end polishing followed by ligation and size selection for library preparation. In some embodiments, the temperature of reaction chamber 440 can be thermal cycle to amplify fragments by polymerase chain reaction. In one embodiment, the reaction is monitored in real time to control the amplification.

In another embodiment, after reverse transcription, the nanodroplets 325 can be broken and the transposon from the Nextera Flex Library Preparation (Illumina) kits can be added to generate libraries. Other biochemical manipulations such as ATAC-Seq, methylation, etc. can be performed in reaction chamber 440. Following optional reactions in reaction chamber 440, the spatially encoded material can be output through spatial encoder output microchannel 430 for additional sample preparation, quality control, or analysis.

Integrated cartridge 4500 can be injection molded with microchannels sealed with a transparent layer by laminating an optical heat seal (ThermoFisher, Catalog number HSF0031), or other material, by ultra sonic welding, glues, adhesives, or other well known means.

As used herein, the following meanings apply unless otherwise specified. As used herein, the following meanings apply unless otherwise specified. The word "may" is used in a permissive sense (i.e., meaning having the potential to), rather than the mandatory sense (i.e., meaning must). The words "include", "including", and "includes" and the like mean including, but not limited to. The singular forms "a," "an," and "the" include plural referents. Thus, for example, reference to "an element" includes a combination of two or more elements, notwithstanding use of other terms and phrases for one or more elements, such as "one or more." As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. The term "or" is, unless indicated otherwise, non-exclusive, i.e., encompassing both "and" and "or." Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present). Both plural and singular means may be included. The term "any of" between a modifier and a sequence means that the modifier modifies each member of the sequence. So, for example, the phrase "at least any of 1, 2 or 3" means "at least 1, at least 2 or at least 3". The term "consisting essentially of" refers to the inclusion of recited elements and other elements that do not materially affect the basic and novel characteristics of a claimed combination.

It will be readily apparent to one of ordinary skill in the art that the embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

All patents, patent applications, published applications, treatises and other publications referred to herein, both supra and infra, are incorporated by reference in their entirety. If a definition and/or description is set forth herein that is contrary to or otherwise inconsistent with any definition set forth in the patents, patent applications, published applications, and other publications that are herein incorporated by reference, the definition and/or description set forth herein prevails over the definition that is incorporated by reference.

What is claimed is:

1. A method comprising:
   a) providing a frozen biological tissue specimen on a sample carrier, wherein cells in the tissue sample have a spatial position in the tissue specimen, and wherein the sample carrier comprises (i) a perforated support that supports the tissue specimen and (ii) an array of passages at addressable positions through the sample carrier and positioned below the perforated support;
   b) disrupting the tissue specimen to release one or a plurality of cells or nuclei; and
   c) collecting a microsample comprising the one or a plurality of released cells or nuclei through the perforations into the passages, wherein the addressable position of a passage indicates the original spatial position of the one or a plurality of cells or nuclei moved into the passage.

2. The method of claim 1, further comprising determining biomolecular information from the one or a plurality of cells or nuclei collected in each passage, wherein the information is selected from proteomic information, nucleic acid sequence information, and epigenetic information.

3. The method of claim 1, further comprising creating a 2-D or 3-D map of the tissue specimen indicating spatial position of biomolecular information of the tissue (selected from proteomic information, nucleic acid sequence information, and epigenetic information.

4. The method of claim 2, further comprising:
sectioning a frozen tissue specimen into a plurality of slices;
processing each slice according to operation (a) through (c);
generating biomolecules from one or more microregions of each slice; and
producing a 3-D reconstruction of spatial position of the biomolecular information in the original tissue specimen.

5. The method of claim 1, further comprising encoding biomolecules collected from one or a plurality of cells or nuclei from each spatial position with positional information tags that indicate the original spatial position of the biomolecules in the tissue specimen.

6. The method of claim 1, further comprising delivering collected single cells or nuclei in boluses into a single flow stream, wherein a position of a bolus in a train of boluses in the flow stream depends on the original spatial position of the single cells or nuclei in the bolus in the tissue specimen.

7. The method of claim 1, further comprising:
d) delivering collected cells or nuclei into wells of a multi-well plate, wherein the position of the wells into which cells or nuclei are delivered depends on the original spatial position of the cells or nuclei in the bolus in the tissue specimen.

8. The method of claim 1, further comprising:
d) contacting a collected microsample with a solid surface or particle having attached thereto an oligonucleotide comprising an amplification primer and oligonucleotide barcode sequence, wherein the barcode sequence provides information about the original spatial position of the cells or nuclei in the microsample in the tissue specimen.

9. A method comprising:
a) providing a frozen biological tissue specimen on a sample carrier, wherein cells in the tissue specimen have a spatial position in the tissue specimen;
b) delivering, with a microsyringe, tissue disruption solution and or nuclei isolation solution to a microregion of the tissue specimen to release one or a plurality of cells or nuclei;
c) collecting, with a microsyringe, a microsample comprising one or a plurality of released cells or nuclei; and
d) moving the microsyringe with the microsample to a well of multiwell plate or to a spatial encoder module and,
e) delivering the cells or nuclei in the microsample.

10. The method of claim 1, wherein collecting comprises moving cells or nuclei by force exerted by a liquid, into the passages.

11. The method of claim 1, wherein single cells or nuclei are collected per passage.

12. The method of claim 1, wherein single cells or nuclei are collected into passages from a microregion in the tissue specimen having a largest dimension of about 20 microns to about 150 microns.

13. The method of claim 5, wherein the information tag is a barcoded antibody, a barcoded oligonucleotide or a mass tag.

14. The method of claim 1, wherein disrupting tissue into nuclei comprises delivering to the tissue specimen on the platform a solution comprising a detergent.

15. The method of claim 14, wherein the solution is delivered through an array of capillaries positioned above the specimen carrier.

16. The method of claim 1, comprising collecting a single cell nucleus from each microregion.

17. The method of claim 1, further comprising:
d) contacting a collected microsample with spatial barcodes, which spatial barcodes provide information about the original spatial position of the cells or nuclei in the microsample in the tissue specimen.

18. The method of claim 1, further comprising:
d) treating collecting nucleic acids in the cells or nuclei with bisulfite and determining methylation patterns of the bisulfite-treated nucleic acids.

19. The method of claim 9, wherein the microsyringe is controlled by a robotic device.

20. The method of claim 17, wherein the spatial barcodes are comprised in the microsyringe barrel or plunger, or on beads preloaded into the microsyringe.

21. The method of claim 9. comprising moving the microsyringe with the microsample to a well of multiwell plate.

22. The method of claim 9, comprising moving the microsyringe with the microsample to a spatial encoder module.

* * * * *